(12) United States Patent
Ebata et al.

(10) Patent No.: US 12,059,304 B2
(45) Date of Patent: Aug. 13, 2024

(54) ULTRASOUND DIAGNOSTIC APPARATUS, METHOD FOR CONTROLLING ULTRASOUND DIAGNOSTIC APPARATUS, AND PROCESSOR FOR ULTRASOUND DIAGNOSTIC APPARATUS

(71) Applicant: FUJIFILM Corporation, Tokyo (JP)

(72) Inventors: Tetsurou Ebata, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 136 days.

(21) Appl. No.: 17/823,366

(22) Filed: Aug. 30, 2022

(65) Prior Publication Data
US 2022/0409183 A1    Dec. 29, 2022

Related U.S. Application Data

(63) Continuation of application No. PCT/JP2021/008716, filed on Mar. 5, 2021.

(30) Foreign Application Priority Data

Mar. 24, 2020 (JP) .................................. 2020-052324

(51) Int. Cl.
*A61B 8/08* (2006.01)
*A61B 8/00* (2006.01)
*G16H 50/30* (2018.01)

(52) U.S. Cl.
CPC ............ *A61B 8/5223* (2013.01); *G16H 50/30* (2018.01); *A61B 8/463* (2013.01); *G06T 2207/10132* (2013.01)

(58) Field of Classification Search
CPC .................. A61B 8/5223; A61B 8/463; G06T 2207/10132; G16H 50/30
See application file for complete search history.

(56) References Cited

U.S. PATENT DOCUMENTS

2004/0024302 A1  2/2004 Chalana et al.
2010/0198075 A1* 8/2010 McMorrow ............ A61B 8/483
                                                                    600/449
(Continued)

FOREIGN PATENT DOCUMENTS

| JP | 2010-207596 A | 9/2010 |
| JP | 2017-109074 A | 6/2017 |
| WO | 2020/008746 A1 | 1/2020 |

OTHER PUBLICATIONS

International Search Report issued in PCT/JP2021/008716; mailed May 18, 2021.

(Continued)

*Primary Examiner* — Chao Sheng
(74) *Attorney, Agent, or Firm* — Studebaker & Brackett PC

(57) ABSTRACT

An ultrasound diagnostic apparatus (1) includes a urinary bladder extraction unit (9), a feature quantity calculation unit (10), a candidate frame extraction unit (11), and a urine volume measurement unit (13). The urinary bladder extraction unit (9) extracts a urinary bladder region from ultrasound images of a plurality of frames. The feature quantity calculation unit (10) calculates a feature quantity related to the bladder region. The candidate frame extraction unit (11) extracts, from the ultrasound images of the plurality of frames, an ultrasound image of a frame for which the feature quantity becomes a local maximum, as an ultrasound image of at least one candidate frame that serves as a candidate subjected to measurement. The urine volume measurement unit (13) analyzes an ultrasound image of a measurement frame selected from the ultrasound image of the at least one candidate frame to measure a urine volume.

19 Claims, 11 Drawing Sheets

(56) References Cited

U.S. PATENT DOCUMENTS

2017/0164924 A1    6/2017   Urabe et al.
2019/0261846 A1    8/2019   Oh et al.
2021/0077066 A1    3/2021   Imai

OTHER PUBLICATIONS

International Preliminary Report on Patentability (Chapter I) and Written Opinion of the International Searching Authority issued in PCT/JP2021/008716; issued Sep. 22, 2022.
Extended European Search Report issued in EP 21 77 5874.7-1126 by the European Patent Office on Jul. 20, 2023.
An Office Action; "Notice of Reasons for Refusal," mailed by the Japanese Patent Office on Oct. 10, 2023, which corresponds to Japanese Patent Application No. 2022-509491 and is related to U.S. Appl. No. 17/823,366; with English language translation.

* cited by examiner

ULTRASOUND DIAGNOSTIC APPARATUS, METHOD FOR CONTROLLING ULTRASOUND DIAGNOSTIC APPARATUS, AND PROCESSOR FOR ULTRASOUND DIAGNOSTIC APPARATUS

CROSS-REFERENCE TO RELATED APPLICATIONS

This application is a Continuation of PCT International Application No. PCT/JP2021/008716 filed on Mar. 5, 2021, which claims priority under 35 U.S.C. § 119(a) to Japanese Patent Application No. 2020-052324 filed on Mar. 24, 2020. The above application is hereby expressly incorporated by reference, in its entirety, into the present application.

BACKGROUND OF THE INVENTION

1. Field of the Invention

The present invention relates to an ultrasound diagnostic apparatus for measuring a urine volume in a urinary bladder of a subject, a method for controlling the ultrasound diagnostic apparatus, and a processor for the ultrasound diagnostic apparatus.

2. Description of the Related Art

In the related art, an ultrasound diagnostic apparatus is used to observe the urinary bladder of a subject and measure the urine volume in the observed urinary bladder. In general, the urine volume in the urinary bladder of a subject is substantially equal to the volume of the urinary bladder of the subject. Thus, the volume of the urinary bladder of the subject is measured as the urine volume. To perform such urine volume measurement easily, for example, an ultrasound diagnostic apparatus of JP2017-109074A has been developed. In response to a user pressing a trigger button included in the ultrasound diagnostic apparatus of JP2017-109074A in a state in which ultrasound images of a plurality of frames including the urinary bladder of a subject are acquired, the ultrasound diagnostic apparatus automatically selects an ultrasound image of a frame determined to be suitable for urine volume measurement, based on the ultrasound images of the plurality of frames acquired by the user. The ultrasound diagnostic apparatus then measures the urine volume based on the ultrasound image of the selected frame.

SUMMARY OF THE INVENTION

However, the ultrasound diagnostic apparatus of JP2017-109074A may erroneously detect a urinary bladder region included in the ultrasound images and thus may select an ultrasound image of a frame not suitable for urine volume measurement such as a frame in which the diameter of the urinary bladder is erroneously measured. Consequently, the accuracy of urine volume measurement may decrease.

In addition, when the user attempts to manually select an ultrasound image of a frame subjected to urine volume measurement in order to select the ultrasound image of the suitable frame, the user needs to check ultrasound images of a large number of frames. Consequently, there is an issue in that a great deal of labor is required.

The present invention is made to overcome such issues in the related art, and an object thereof is to provide an ultrasound diagnostic apparatus capable of increasing the accuracy of urine volume measurement while reducing a load imposed on a user, a method for controlling the ultrasound diagnostic apparatus, and a processor for the ultrasound diagnostic apparatus.

To achieve the object above, an ultrasound diagnostic apparatus according to the present invention includes an image memory configured to store ultrasound images of a plurality of frames; a urinary bladder extraction unit configured to extract a urinary bladder region from each of the ultrasound images of the plurality of frames; a feature quantity calculation unit configured to calculate a feature quantity related to the urinary bladder region extracted for each of the ultrasound images of the plurality of frames by the urinary bladder extraction unit; a candidate frame extraction unit configured to extract, from the ultrasound images of the plurality of frames, an ultrasound image of a frame for which the feature quantity calculated by the feature quantity calculation unit becomes a local maximum, as an ultrasound image of at least one candidate frame that serves as a candidate subjected to measurement; a measurement frame selection unit configured to select an ultrasound image of a measurement frame that serves as a target subjected to measurement from the ultrasound image of the at least one candidate frame extracted by the candidate frame extraction unit; and a urine volume measurement unit configured to analyze the ultrasound image of the measurement frame selected by the measurement frame selection unit to measure a urine volume.

In a case where a difference between a local maximum value of the feature quantity in the ultrasound image of the frame for which the feature quantity calculated by the feature quantity calculation unit becomes the local maximum and a local minimum value of the feature quantity adjacent to the local maximum value in time series is smaller than a predetermined difference threshold, the candidate frame extraction unit can remove the ultrasound image of the frame for which the feature quantity becomes the local maximum from the ultrasound image of the at least one candidate frame.

Alternatively, the candidate frame extraction unit can remove, from the ultrasound image of the at least one candidate frame, an ultrasound image of a frame having a local maximum value of the feature quantity that is smaller than a feature quantity threshold determined relative to a maximum value of the feature quantity in ultrasound images of frames for each of which the feature quantity calculated by the feature quantity calculation unit becomes a local maximum.

Alternatively, the candidate frame extraction unit can remove, from the ultrasound image of the at least one candidate frame, an ultrasound image of a frame having a local maximum value of the feature quantity that is outside a feature quantity range determined relative to an average value of local maximum values of the feature quantity in ultrasound images of frames for each of which the feature quantity calculated by the feature quantity calculation unit becomes a local maximum.

The ultrasound diagnostic apparatus can further include a monitor configured to display the ultrasound image of the at least one candidate frame extracted by the candidate frame extraction unit.

In this case, the extracted ultrasound image of the at least one candidate frame can include extracted ultrasound images of one or more candidate frames, and the candidate frame extraction unit can calculate, as an index value, a roundness of the urinary bladder region or an edge clarity of the urinary bladder region for each of the extracted ultrasound images of the one or more candidate frames, sort the ultrasound images of the one or more candidate frames based on the calculated index value, and cause the monitor to display the sorted ultrasound images of the one or more candidate frames.

The extracted ultrasound image of the at least one candidate frame can include extracted ultrasound images of one or more candidate frames, and the candidate frame extraction unit can cause the monitor to display each of the extracted ultrasound images of the one or more candidate frames and a graph that represents a time-series change in the feature quantity and in which a marker representing a time-series position corresponding to the ultrasound image of the candidate frame is placed.

The extracted ultrasound image of the at least one candidate frame can include extracted ultrasound images of one or more candidate frames, and the candidate frame extraction unit can cause the monitor to display each of the extracted ultrasound images of the one or more candidate frames and a value of the feature quantity corresponding to the ultrasound image of the candidate frame.

The ultrasound diagnostic apparatus can further include an input device with which the user performs an input operation. In this case, the measurement frame selection unit can select, as the ultrasound image of the measurement frame, an ultrasound image of a frame selected by the user via the input device from the ultrasound image of the at least one candidate frame displayed on the monitor.

Alternatively, the ultrasound diagnostic apparatus can include an input device with which the user performs an input operation. In this case, the measurement frame selection unit can determine whether or not ultrasound images of a plurality of candidate frames are extracted by the candidate frame extraction unit, in a case of determining that ultrasound images of a plurality of candidate frames are extracted by the candidate frame extraction unit, select, as the ultrasound image of the measurement frame, an ultrasound image of a frame selected by the user via the input device from the ultrasound images of the plurality of candidate frames displayed on the monitor, and in a case of determining that an ultrasound image of only one candidate frame is extracted by the candidate frame extraction unit, select the ultrasound image of the only one candidate frame as the ultrasound image of the measurement frame.

A method for controlling an ultrasound diagnostic apparatus according to the present invention includes extracting a urinary bladder region from each of ultrasound images of a plurality of frames; calculating a feature quantity related to the urinary bladder region extracted for each of the ultrasound images of the plurality of frames; extracting, from the ultrasound images of the plurality of frames, an ultrasound image of a frame for which the calculated feature quantity becomes a local maximum, as an ultrasound image of at least one candidate frame that serves as a candidate subjected to measurement; selecting an ultrasound image of a measurement frame that serves as a target subjected to measurement from the ultrasound image of the at least one candidate frame; and analyzing the selected ultrasound image of the measurement frame to measure a urine volume.

A processor for an ultrasound diagnostic apparatus according to the present invention is configured to extract a urinary bladder region from each of ultrasound images of a plurality of frames; calculate a feature quantity related to the urinary bladder region extracted for each of the ultrasound images of the plurality of frames; extract, from the ultrasound images of the plurality of frames, an ultrasound image of a frame for which the calculated feature quantity becomes a local maximum, as an ultrasound image of at least one candidate frame that serves as a candidate subjected to measurement; select an ultrasound image of a measurement frame that serves as a target subjected to measurement from the ultrasound image of the at least one candidate frame; and analyze the selected ultrasound image of the measurement frame to measure a urine volume.

According to the present invention, the ultrasound diagnostic apparatus includes the urinary bladder extraction unit that extracts a urinary bladder region from each of ultrasound images of a plurality of frames; the feature quantity calculation unit that calculates a feature quantity related to the urinary bladder region extracted for each of the ultrasound images of the plurality of frames by the urinary bladder extraction unit; the candidate frame extraction unit that extracts, from the ultrasound images of the plurality of frames, an ultrasound image of a frame for which the feature quantity calculated by the feature quantity calculation unit becomes a local maximum, as an ultrasound image of at least one candidate frame that serves as a candidate subjected to measurement; the measurement frame selection unit that selects an ultrasound image of a measurement frame that serves as a target subjected to measurement from the ultrasound image of the at least one candidate frame extracted by the candidate frame extraction unit; and the urine volume measurement unit that analyzes the ultrasound image of the measurement frame selected by the measurement frame selection unit to measure a urine volume. Thus, the ultrasound diagnostic apparatus can increase the accuracy of urine volume measurement while reducing the load imposed on a user.

DESCRIPTION OF THE PREFERRED EMBODIMENTS

Embodiments of this invention will be described below with reference to the accompanying drawings.

The description of constituent elements below is given based on representative embodiments of the present invention. However, the present invention is not limited to such embodiments.

In the present specification, a numerical range expressed using "to" means a range including a numerical value preceding "to" as a lower limit value and a numerical value following "to" as an upper limit value.

In the present specification, the terms "identical" and "same" include an error range generally acceptable in the technical field.

First Embodiment

Figure 1:
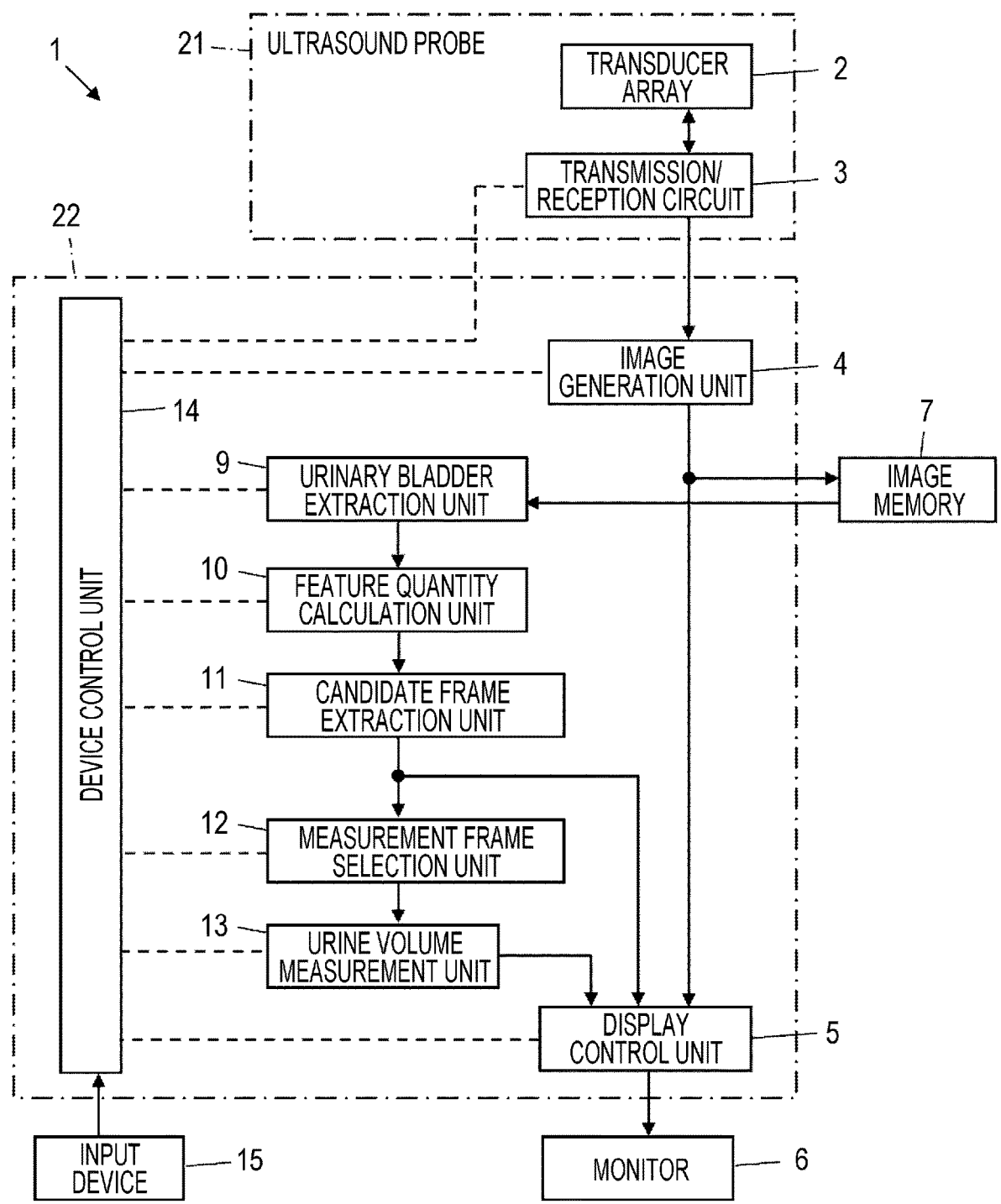
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 includes a transducer array 2. A transmission/reception circuit 3, an image generation unit 4, a display control unit 5, and a monitor 6 are sequentially connected to the transducer array 2. The transducer array 2 and the transmission/reception circuit 3 are included in an ultrasound probe 21. An image memory 7 is connected to the image generation unit 4. A urinary bladder extraction unit 9, a feature quantity calculation unit 10, a candidate frame extraction unit 11, a measurement frame selection unit 12, and a urine volume measurement unit 13 are sequentially connected to the image memory 7. The candidate frame extraction unit 11 and the urine volume measurement unit 13 are connected to the display control unit 5.

A device control unit 14 is connected to the transmission/reception circuit 3, the image generation unit 4, the display control unit 5, the urinary bladder extraction unit 9, the feature quantity calculation unit 10, the candidate frame extraction unit 11, the measurement frame selection unit 12, and the urine volume measurement unit 13. An input device 15 is connected to the device control unit 14.

The image generation unit 4, the display control unit 5, the urinary bladder extraction unit 9, the feature quantity calculation unit 10, the candidate frame extraction unit 11, the measurement frame selection unit 12, the urine volume measurement unit 13, and the device control unit 14 constitute a processor 22 for the ultrasound diagnostic apparatus 1.

The transducer array 2 of the ultrasound probe 21 illustrated in FIG. 1 has a plurality of transducers arranged one-dimensionally or two-dimensionally. Each of these transducers transmits an ultrasonic wave in accordance with a drive signal supplied from the transmission/reception circuit 3. Each of these transducers also receives an ultrasonic echo from the subject, and outputs a signal based on the ultrasonic echo. Each of the transducers is configured by forming electrodes at respective ends of a piezoelectric body made of, for example, a piezoelectric ceramic represented by lead zirconate titanate (PZT), a polymer piezoelectric element represented by polyvinylidene difluoride (PVDF), and a piezoelectric single crystal represented by lead magnesium niobate-lead titanate (PMN-PT).

Figure 2:
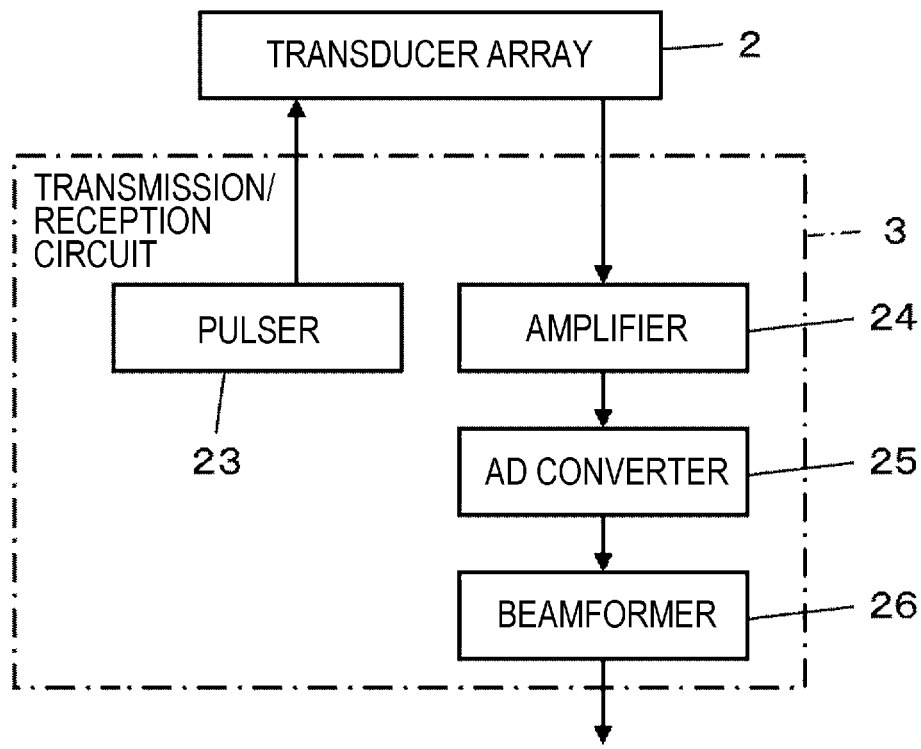
FIG. 2 is a block diagram illustrating an internal configuration of a transmission/reception circuit in the first embodiment of the present invention.

Under the control of the device control unit 14, the transmission/reception circuit 3 transmits ultrasonic waves from the transducer array 2, and generates a sound ray signal based on reception signals acquired by the transducer array 2. As illustrated in FIG. 2, the transmission/reception circuit 3 has a pulser 23 connected to the transducer array 2, and an amplifier 24, an analog-to-digital (AD) converter 25, and a beamformer 26 sequentially connected in series from the transducer array 2.

The pulser 23 includes, for example, a plurality of pulse generators. The pulser 23 adjusts delay amounts of respective drive signals, based on a transmission delay pattern selected in accordance with a control signal from the device control unit 14 so that ultrasonic waves transmitted from the plurality of transducers of the transducer array 2 form an ultrasonic beam, and supplies the resulting drive signals to the respective transducers. As described above, in response to application of a pulsed or continuous-wave voltage to the electrodes of the transducers of the transducer array 2, the piezoelectric body expands and contracts. Consequently, pulsed or continuous-wave ultrasonic waves are generated from the respective transducers, and an ultrasonic beam is formed from a composite wave of those ultrasonic waves.

The transmitted ultrasonic beam is reflected by a target such as a part of a subject, for example, and propagates toward the transducer array 2 of the ultrasound probe 21. An ultrasonic echo propagating toward the transducer array 2 in this manner is received by each of the transducers of the transducer array 2. At this time, in response to receipt of the propagating ultrasonic echo, the transducers of the transducer array 2 expand and contract to generate respective reception signals, which are electric signals, and output these reception signals to the amplifier 24.

The amplifier 24 amplifies a signal input from each of the transducers of the transducer array 2, and transmits the amplified signal to the AD converter 25. The AD converter 25 converts the signals transmitted from the amplifier 24 into pieces of digital reception data, and transmits these pieces of reception data to the beamformer 26. The beamformer 26 performs so-called reception focusing processing in which the pieces of reception data obtained by the AD converter 25 through conversion are given respective delays and then are added in accordance with sonic velocities or a sonic velocity distribution set based on a reception delay pattern selected in accordance with the control signal from the device control unit 14. Through this reception focusing processing, the pieces of reception data obtained by the AD converter 25 through the conversion are subjected to phasing addition, and a sound ray signal to which the focus of the ultrasonic echo converges is acquired.

Figure 3:
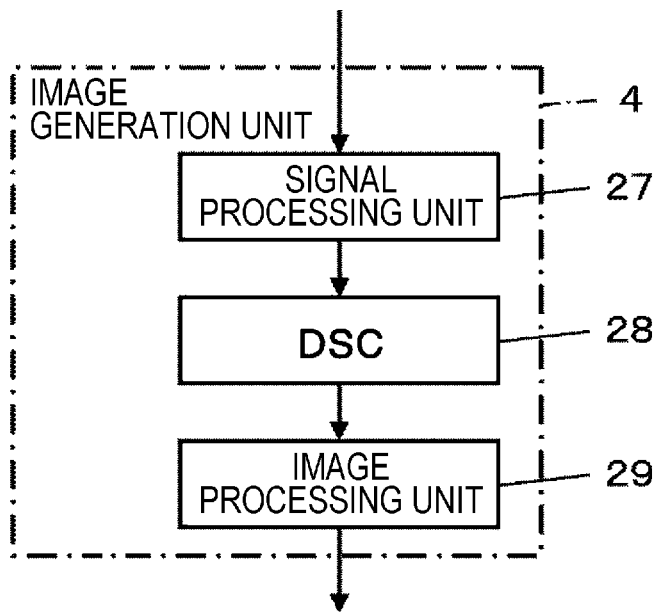
FIG. 3 is a block diagram illustrating an internal configuration of an image generation unit in the first embodiment of the present invention.

As illustrated in FIG. 3, the image generation unit 4 has a configuration in which a signal processing unit 27, a digital scan converter (DSC) 28, and an image processing unit 29 are sequentially connected in series.

In accordance with a depth of a reflected position of the ultrasonic waves, the signal processing unit 27 performs distance-based attenuation correction on the sound ray signal generated by the beamformer 26 of the transmission/reception circuit 3, and then performs envelope detection processing. In this manner, the signal processing unit 27 generates a B-mode image signal, which is tomographic image information related to a tissue in the subject.

The DSC 28 converts (raster-converts) the B-mode image signal generated by the signal processing unit 27 into an image signal according to a normal television signal scanning method.

The image processing unit 29 performs various kinds of necessary image processing such as grayscale processing on the B-mode image signal input from the DSC 28, and then outputs the B-mode image signal to the display control unit 5 and the image memory 7. Hereinafter, the B-mode image signal on which the image processing has been performed by the image processing unit 29 is simply referred to as an ultrasound image.

The image memory 7 is a memory that stores ultrasound images of a series of frames generated by the image generation unit 4 for each diagnosis. The image memory 7 to be used may be a recording medium such as a flash memory, a hard disc drive (HDD), a solid state drive (SDD), a flexible disc (FD), a magneto-optical disc (MO), a magnetic tape (MT), a random access memory (RAM), a compact disc (CD), a digital versatile disc (DVD), a secure digital (SD) card, or a Universal Serial Bus (USB) memory; a server; or the like.

Figure 4:
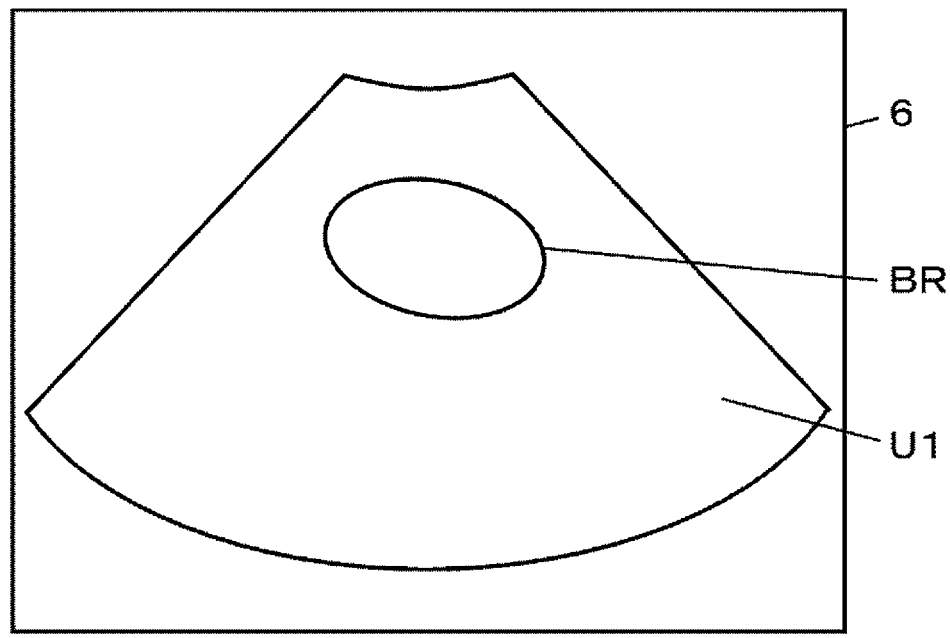
FIG. 4 is a diagram schematically illustrating an example of an ultrasound image including a urinary bladder region in the first embodiment of the present invention.

For example, as illustrated in FIG. 4, the urinary bladder extraction unit 9 extracts a urinary bladder region BR from an ultrasound image U1. For example, the urinary bladder extraction unit 9 can use a technique using deep learning described in Krizhevsk et al.: ImageNet Classification with Deep Convolutional Neural Networks, Advances in Neural Information Processing Systems 25, pp. 1106-1114 (2012) to extract the urinary bladder region BR in the ultrasound image U1. Alternatively, the urinary bladder extraction unit 9 can use, as another technique, a known technique such as graph cut (Y. Boykov and V. Kolmogorov, "An experimental comparison of min-cut/max-flow algorithm for energy minimization in vision", IEEE Transactions on Pattern Analysis and Machine Intelligence, 26, 9, pp. 1123-1137, 2004), Snakes (A. W. Michael Kass and D. Terzopoulos: "Snakes: Active contour models", Int. J. Computer Vision, 1, 4, pp. 321-331, 1988), or Level Sets (M. Sussman, P. Smereka, and S. Osher: "A level set approach for computing solutions to incompressible two-phase flow", J. Comput. Phys, 114, 1, pp. 146-159, 1994) to extract the urinary bladder region BR.

The feature quantity calculation unit 10 calculates a feature quantity related to the extracted urinary bladder region BR in the ultrasound image U1 from which the urinary bladder region BR has been extracted by the urinary bladder extraction unit 9. Through image analysis, the feature quantity calculation unit 10 can calculate, as the feature quantity, an area of the extracted urinary bladder region BR, for example. Through image analysis, the feature quantity calculation unit 10 can calculate, as the feature quantity, the largest diameters of the urinary bladder region BR in three directions orthogonal to each other, which are used for measuring the volume of the urinary bladder described below, for example. Through image analysis, the feature quantity calculation unit 10 can calculate, as the feature quantity, the largest diameter in any direction of the extracted urinary bladder region BR, the circumferential length of the urinary bladder region BR, or the like.

When the image generation unit 4 generates ultrasound images of frames including the urinary bladder region BR of the subject, the user usually scans the urinary bladder by changing the position or angle of the ultrasound probe 21 while keeping the ultrasound probe 21 in contact with the body surface of the subject. At this time, the user can scan the urinary bladder by using, for example, a swing method in which the ultrasound probe 21 is inclined on the body surface of the subject while the position of the ultrasound probe 21 is fixed.

Figure 5:
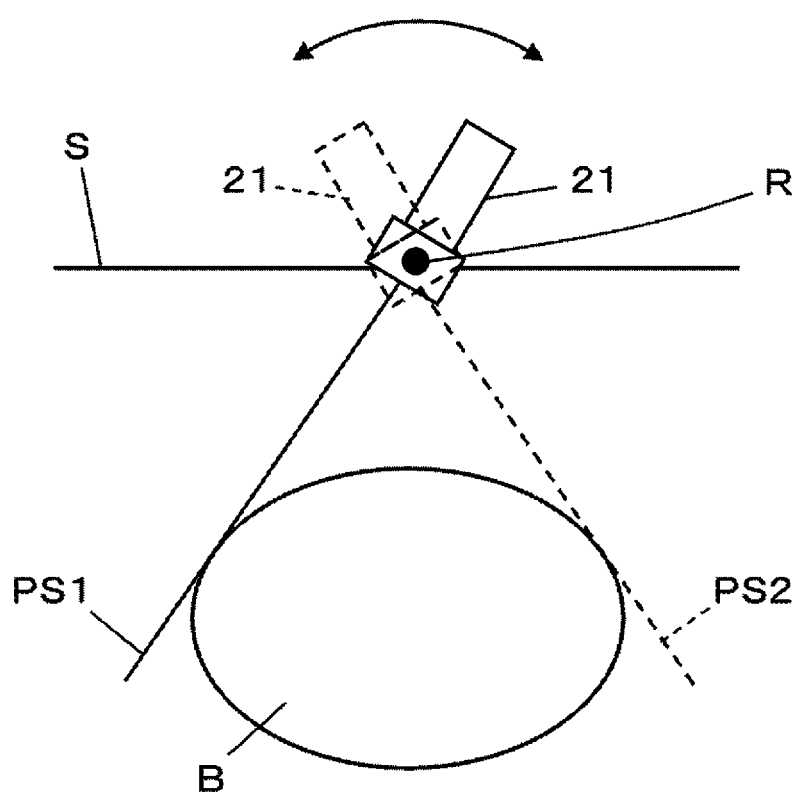
FIG. 5 is a diagram schematically illustrating how a urinary bladder is scanned using a swing method.

When the user scans the urinary bladder using the swing method, the user inclines the ultrasound probe 21 on a body surface S of the subject back and forth between an inclination angle at which a scan cross-section PS1 that passes through one end of a urinary bladder B is imaged and an inclination angle at which a scan cross-section PS2 that passes through the other end of the urinary bladder B with respect to a rotational axis R that is parallel to the arrangement direction of the transducer array 2 as illustrated in FIG. 5, for example.

Figure 6:
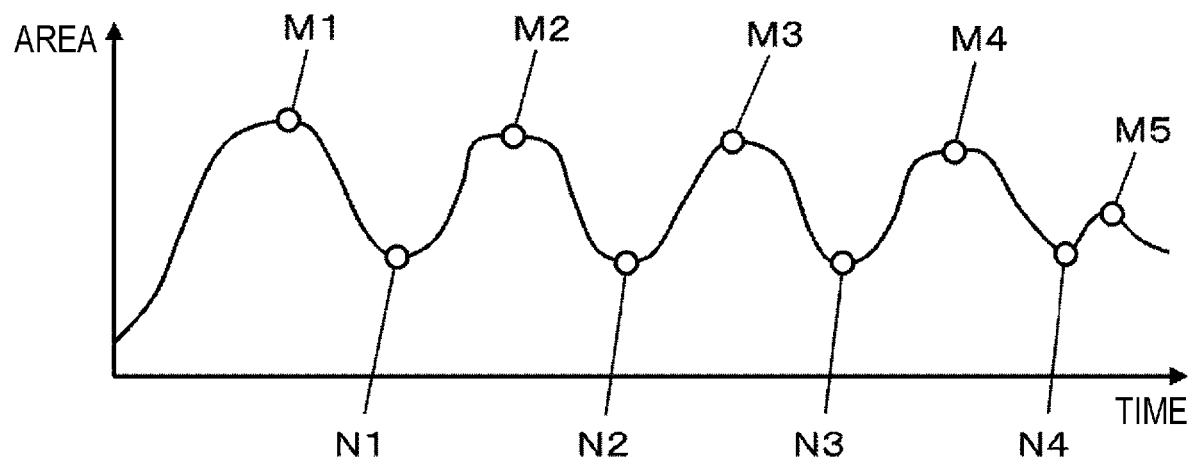
FIG. 6 is a diagram illustrating an example of a time-series change of an area of a urinary bladder region in the first embodiment of the present invention.

At this time, the value of the area of the urinary bladder region BR included in the ultrasound images of the frames consecutively generated by the image generation unit 4 changes in time series such that the value alternately has a local maximum value and a local minimum value as illustrated in FIG. 6, for example. The example of FIG. 6 presents a relationship between the area of the urinary bladder region BR and the generation time of the ultrasound image of the frame for which the area of the urinary bladder region BR is calculated, and the value of the area of the urinary bladder region BR changes in time series to have five local maximum values M1 to M5 and four local minimum values N1 to N4. While the example of FIG. 6 presents the time-series change of the value of the area of the urinary bladder region BR, the largest diameter of the urinary bladder region BR also shows a time-series change as illustrated in FIG. 6.

Figure 7:
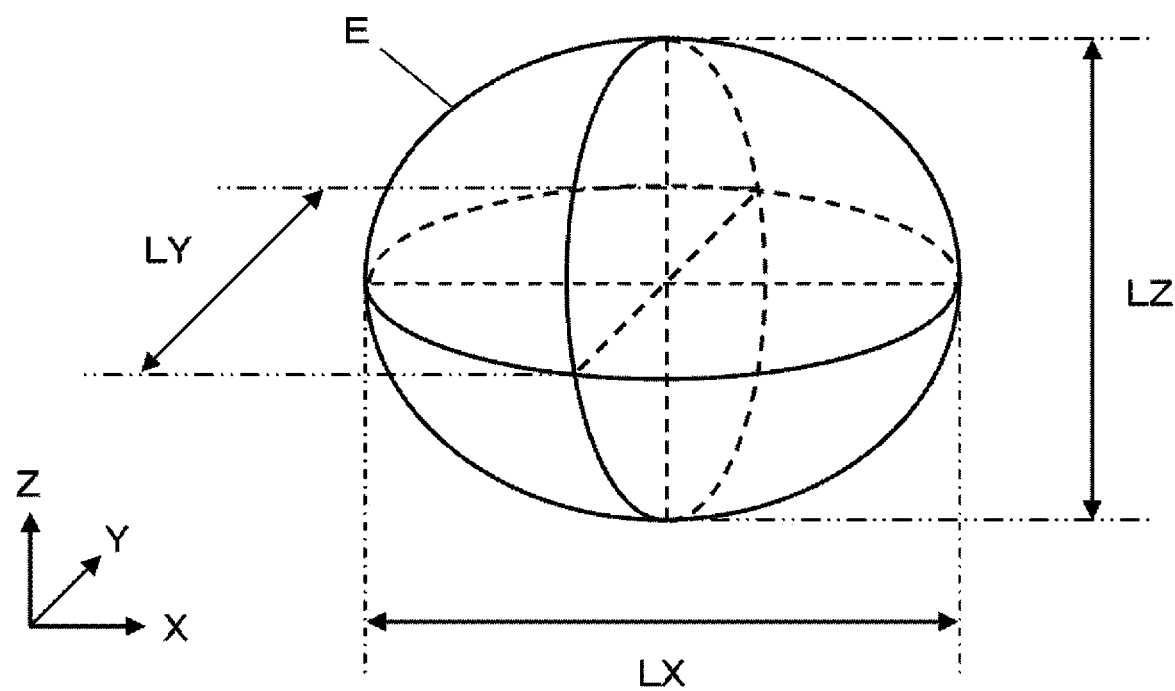
FIG. 7 is a diagram illustrating an example of an ellipsoid.

In general, the urinary bladder B of the subject usually has a substantially ellipsoidal shape. Thus, the urine volume in the urinary bladder B is measured by calculating the volume of the urinary bladder B while the urinary bladder B is regarded as an ellipsoid. As illustrated in FIG. 7, when an ellipsoid E has a symmetrical shape with respect to an XY plane, an YZ plane, and an XZ plane, it is known that the volume of the ellipsoid E is calculated by $(LX \times LY \times LZ) \times \pi/6$, where LX is the largest diameter of the ellipsoid E in the X direction, LY is the largest diameter of the ellipsoid E in the Y direction, LZ is the largest diameter of the ellipsoid E in the Z direction, and $\pi$ is the circumference ratio. Thus, when the volume of the urinary bladder B is calculated using an ultrasound image, it is desirable to perform measurement on ultrasound images of two frames corresponding to scan cross-sections that pass through the center of the urinary bladder B and are orthogonal to each other.

As described above, the ultrasound image of the frame that corresponds to a scan cross-section that passes through the center of the urinary bladder B is an ultrasound image of a frame for which the feature quantities such as the area and the largest diameter of the urinary bladder region BR become a local maximum in the time-series change when the urinary bladder B is scanned using the swing method, for example.

The candidate frame extraction unit 11 extracts ultrasound images of frames for which the feature quantity calculated by the feature quantity calculation unit 10 for each of the ultrasound images of the plurality of frames stored in the image memory 7 becomes a local maximum, as ultrasound images of candidate frames that serve as measurement candidates of urine volume measurement. In the example of FIG. 6, the candidate frame extraction unit 11 extracts ultrasound images of five frames for which the value of the area of the urinary bladder region BR is the local maximum values M1 to M5, as the ultrasound images of the candidate frames.

Figure 8:
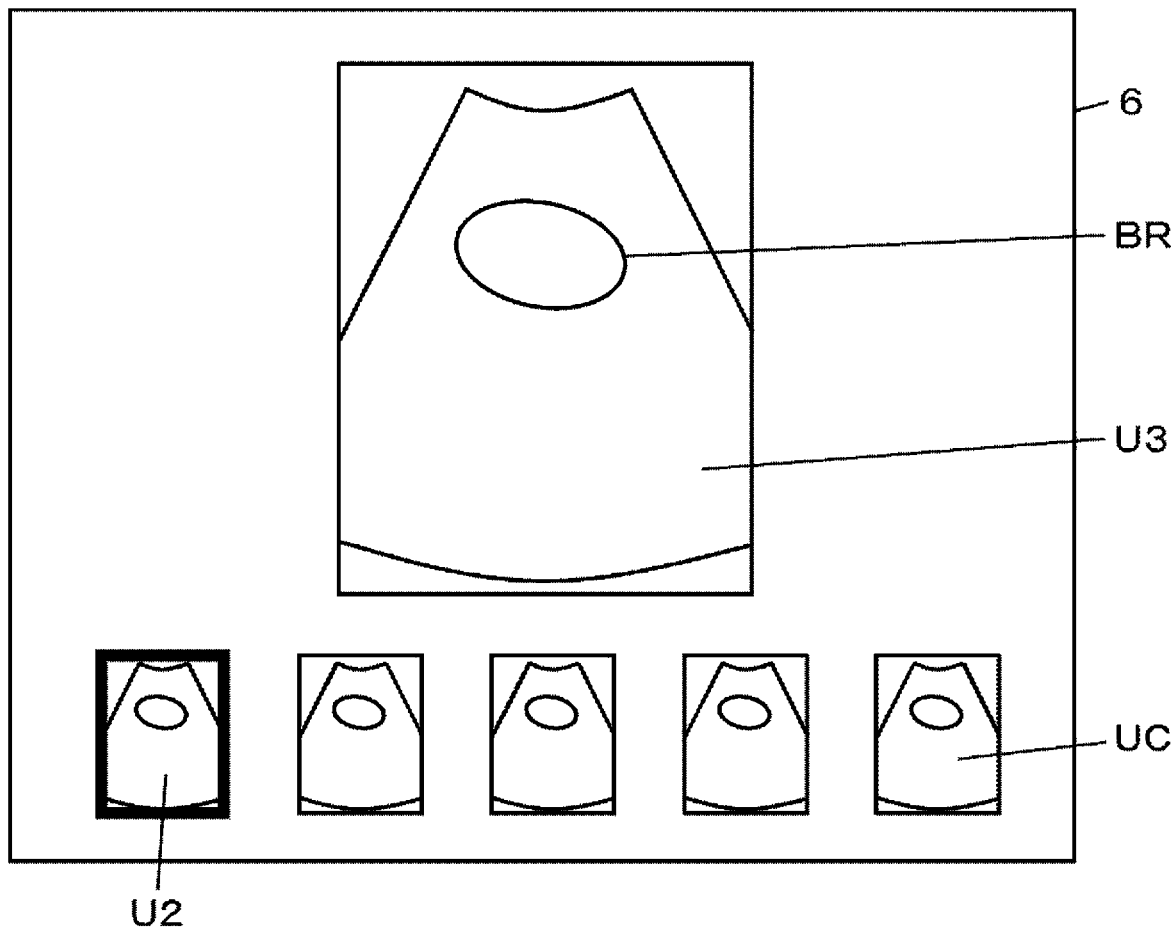
FIG. 8 is a diagram schematically illustrating an example of ultrasound images of a plurality of candidate frames displayed in the first embodiment of the present invention.

For example, as illustrated in FIG. 8, the candidate frame extraction unit 11 causes the monitor 6 to display an extracted ultrasound image UC of at least one candidate frame. In the example illustrated in FIG. 8, ultrasound images UC of five candidate frames are displayed in a lower portion of the monitor 6. When the ultrasound images UC of the plurality of candidate frames are extracted, the candidate frame extraction unit 11 can display the extracted ultrasound images UC of all the candidate frames together on the monitor 6. The candidate frame extraction unit 11 can also display only some of the extracted ultrasound images UC of all the candidate frames together on the monitor 6 in so-called scroll display.

The input device 15 is a device with which a user performs an input operation, and can include a keyboard, a mouse, a trackball, a touch pad, a touch panel, and the like.

The measurement frame selection unit 12 selects, as a measurement frame that serves as a target subjected to measurement, an ultrasound image of a frame selected by the user via the input device 15 from the ultrasound image UC of the at least one candidate frame displayed on the monitor 6. For example, in FIG. 8, an ultrasound image U2 of a frame selected by the user from among the ultrasound images UC of the five candidate frames displayed in the lower portion of the monitor 6 is displayed with a thick frame, and the ultrasound image U2 of this frame is selected as the ultrasound image of the measurement frame by the measurement frame selection unit 12.

The urine volume measurement unit 13 calculates the volume of the urinary bladder B of the subject based on the ultrasound image of the measurement frame selected by the measurement frame selection unit 12 to measure the urine volume in the urinary bladder B. For example, when ultrasound images of two measurement frames corresponding to scan cross-sections that pass through the center of the urinary bladder B and are orthogonal to each other are selected by the measurement frame selection unit 12, the urine volume measurement unit 13 measures lengths of the urinary bladder region BR in the ultrasound images of the two measurement frames, acquires the largest diameters LX, LY, and LZ in the three directions orthogonal to each other, and calculate $(LX \times LY \times LZ) \times \pi/6$. In this manner, the urine volume measurement unit 13 can calculate the volume of the urinary bladder B of the subject.

Under the control of the device control unit 14, the display control unit 5 performs predetermined processing on the ultrasound images of the frames stored in the image memory 7, the ultrasound image UC of at least one candidate frame extracted by the candidate frame extraction unit 11, and information indicating the value of the urine volume in the urinary bladder of the subject measured by the urine volume measurement unit 13, and displays the images and the information on the monitor 6.

Under the control of the display control unit 5, the monitor 6 displays the ultrasound images of the frames generated by the image generation unit 4, the ultrasound images of the frames stored in the image memory 7, the ultrasound image UC of the at least one candidate frame, the value of the urine volume in the urinary bladder of the subject, and the like. The monitor 6 includes a display device such as a liquid crystal display (LCD) or an organic electroluminescence (EL) display, for example.

The device control unit 14 controls each unit of the ultrasound diagnostic apparatus 1, based on a control program or the like stored in advance.

The processor 22 having the image generation unit 4, the display control unit 5, the urinary bladder extraction unit 9, the feature quantity calculation unit 10, the candidate frame extraction unit 11, the measurement frame selection unit 12, the urine volume measurement unit 13, and the device control unit 14 may be constituted by a central processing unit (CPU) and a control program for causing the CPU to perform various processes. However, the processor 22 may be constituted using a field programmable gate array (FPGA), a digital signal processor (DSP), an application specific integrated circuit (ASIC), a graphics processing unit (GPU), or another integrated circuit (IC), or any combination of these.

The image generation unit 4, the display control unit 5, the urinary bladder extraction unit 9, the feature quantity calculation unit 10, the candidate frame extraction unit 11, the measurement frame selection unit 12, the urine volume measurement unit 13, and the device control unit 14 of the processor 22 may be partially or entirely integrated into a single CPU or the like.

An operation of the ultrasound diagnostic apparatus 1 according to the first embodiment will be described in detail below with reference to a flowchart illustrated in FIG. 9.

First, in step S1, an ultrasound image is generated with the ultrasound probe 21 being kept in contact with the body surface S of the subject by the user, and the generated ultrasound image is displayed on the monitor 6. At this time, an ultrasonic beam is transmitted from the plurality of transducers of the transducer array 2 into the subject in accordance with drive signals from the pulser 23 of the transmission/reception circuit 3. The transducers receive an ultrasound echo from the subject and output respective reception signals to the amplifier 24 of the transmission/reception circuit 3. The reception signals are amplified by the amplifier 24, are subjected to AD conversion by the AD converter 25, and are then subjected to phasing addition by the beamformer 26, so that a sound ray signal is generated. In the image generation unit 4, this sound ray signal is subjected to envelope detection processing by the signal processing unit 27 to be a B-mode image signal, and the B-mode image signal is output to the display control unit 5 through the DSC 28 and the image processing unit 29. Consequently, the ultrasound image U1 is displayed on the monitor 6 under the control of the display control unit 5 as illustrated in FIG. 4.

At this time, the user adjusts the position and the inclination of the ultrasound probe 21 while checking the ultrasound image U1 displayed on the monitor 6 so that the urinary bladder region BR of the subject is depicted in the ultrasound image U1.

Next, in step S2, it is determined whether or not a measurement mode for measuring the urine volume in the urinary bladder of the subject is started. For example, when an instruction for starting the measurement mode is given by the user via the input device 15, it is determined that the measurement mode is started. When an instruction for starting the measurement mode is not given by the user, it is determined that the measurement mode is not started. If it is determined that the measurement mode is not started, the process returns to step S1, in which an ultrasound image is generated and displayed. If it is determined that the measurement mode is started in response to the user giving an instruction for starting the measurement mode after adjusting the position of the ultrasound probe 21, the process proceeds to step S3.

If it is determined in step S2 that the measurement mode is started, an ultrasound image is generated as in step S1 and the generated ultrasound image is stored in the image memory 7 in step S3. For example, the user scans the urinary bladder B using the swing method in which the urinary bladder B of the subject is imaged while an inclination of the ultrasound probe 21 is changed.

In subsequent step S4, it is determined whether or not scanning of the urinary bladder B of the subject is ended. For example, when an instruction for ending scanning of the urinary bladder B is given by the user via the input device 15, it is determined that scanning of the urinary bladder B is ended. When an instruction for ending scanning of the urinary bladder B is not given by the user, it is determined that scanning of the urinary bladder B continues. If it is determined that scanning of the urinary bladder B continues, the process returns to step S3, in which an ultrasound image is generated and stored. In this manner, steps S3 and S4 are repeated while scanning of the urinary bladder B continues. Consequently, ultrasound images of a plurality of frames are stored in the image memory 7. If it is determined that scanning of the urinary bladder B is ended, the process proceeds to step S5.

In step S5, the urinary bladder extraction unit 9 performs image analysis on each of the ultrasound images of the plurality of frames stored in the image memory 7, and extracts the urinary bladder region BR representing the urinary bladder B of the subject. Information of the extracted urinary bladder region BR and the ultrasound images of the plurality of frames are sent to the feature quantity calculation unit 10.

In step S6, based on the urinary bladder region BR extracted in step S5 from each of the ultrasound images of the plurality of frames, the feature quantity calculation unit 10 calculates, as a feature quantity related to the urinary bladder region BR, the area of the urinary bladder region BR. Since the user scans the urinary bladder B using the swing method in step S3, the area of the urinary bladder region BR calculated in step S6 changes in time series as illustrated in FIG. 6, for example. The information of the calculated area of the urinary bladder region BR and the ultrasound images of the plurality of frames are sent to the candidate frame extraction unit 11.

The urine volume in the urinary bladder B is measured by calculating the volume of the urinary bladder B while regarding the urinary bladder B to be the ellipsoid E. Thus, ultrasound images of frames corresponding to the scan cross-sections that pass through the center of the urinary bladder B are desirably used as the ultrasound images of the frames used in urine volume measurement. The ultrasound images of such frames are ultrasound images of frames for which the feature quantity of the urinary bladder region BR becomes a local maximum in the time-series change illustrated in FIG. 6.

Thus, in step S7, the candidate frame extraction unit 11 extracts, as candidate ultrasound images UC of candidate frames, ultrasound images of frames for which the area of the urinary bladder region BR that is calculated in step S6 for each of the ultrasound images of the plurality of frames and is received from the feature quantity calculation unit 10 becomes a local maximum. In the example of FIG. 6, the candidate frame extraction unit 11 extracts, as the ultrasound images UC of the candidate frames, ultrasound images of five frames for which the area of the urinary bladder region BR takes the local maximum values M1 to M5.

In step S7, the candidate frame extraction unit 11 displays the extracted ultrasound images UC of the five candidate frames on the monitor 6 as illustrated in FIG. 8, for example. In the example of FIG. 8, the ultrasound images UC of the five candidate frames are displayed in the lower portion of the monitor 6.

In step S8, the user selects the ultrasound image U2 of one frame from among the ultrasound images UC of the five candidate frames displayed on the monitor 6 via the input device 15 as illustrated in FIG. 8. The ultrasound image U2 of the frame selected by the user is selected as the ultrasound image of the measurement frame by the measurement frame selection unit 12. In FIG. 8, the ultrasound image U2 of the frame indicated by a thick frame is selected by the user and is selected as the measurement frame by the measurement frame selection unit 12. At this time, for example, an ultrasound image U3 obtained by enlarging the ultrasound image U2 of the selected frame can be displayed on the monitor 6 to allow the user to easily check the ultrasound image U2 of the selected frame.

The ultrasound image U2 of the frame selected by the user is selected as the ultrasound image of the measurement frame from the ultrasound image UC of the at least one candidate frame displayed on the monitor 6 in this manner. Thus, even if there is an ultrasound image of a frame in which the urinary bladder region BR is not correctly extracted in step S5 for some reason and the ultrasound image of this frame is included in the ultrasound images UC of the plurality of candidate frames extracted in step S7 because the feature quantity in the ultrasound image of this frame takes a local maximum value, the ultrasound image of the measurement frame can be selected from among the ultrasound images of the frames in which the urinary bladder region BR is correctly extracted. Consequently, the accuracy of urine volume measurement can be increased. Since the ultrasound image UC of the at least one candidate frame is automatically extracted based on the feature quantity related to the urinary bladder region BR from among the ultrasound images of the frames stored in the image memory 7, the user need not check ultrasound images of many frames. Consequently, the load imposed on the user in selecting the ultrasound image of the measurement frame can be reduced.

In step S9, it is determined whether or not ultrasound images of two measurement frames corresponding to two scan cross-sections of the urinary bladder B of the subject orthogonal to each other is selected in step S8 in order to measure the urine volume in the urinary bladder B. In step S8 that has already been completed, only an ultrasound image of the measurement frame corresponding to one of the two scan cross-sections of the urinary bladder B orthogonal to each other has been acquired. Thus, it is determined that ultrasound images of two measurement frames corresponding to the two scan cross-sections of the urinary bladder B of the subject orthogonal to each other are not selected, the process returns to step S3, in which scanning of the urinary bladder B is resumed. At this time, the user rotates the orientation of the ultrasound probe 21 by 90 degrees and scans the urinary bladder B.

In steps S3 and S4, an ultrasound image is repeatedly generated and stored unless the user gives an instruction for ending scanning of the urinary bladder B. In response to the user giving the instruction for ending scanning of the urinary bladder B in step S4, the process proceeds to step S5. Description of the subsequent processing of steps S5 to S8 is omitted since the details thereof are identical to those already described.

In step S8, the ultrasound image U2 of the frame selected by the user is selected as the ultrasound image of the measurement frame from the ultrasound image UC of the at least one candidate frame displayed on the monitor 6. The process then proceeds to step S9.

In step S9, it is determined whether or not the ultrasound images of the two measurement frames corresponding to the two scan cross-sections orthogonal to each other of the urinary bladder B of the subject are selected in step S8. In step S8 performed for the second time, the ultrasound image of the second measurement frame is selected. Thus, it is determined that the ultrasound images of the two measurement frames corresponding to the two scan cross-sections of the urinary bladder B of the subject orthogonal to each other are selected, and the process proceeds to step S10.

Figure 10:
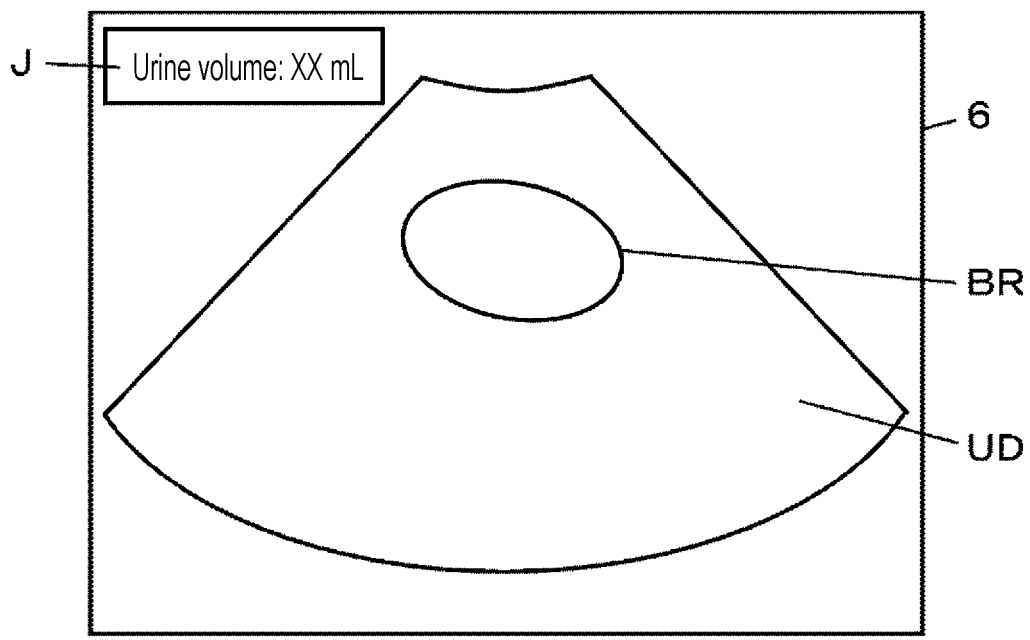
FIG. 10 is a diagram schematically illustrating an example in which a urine volume in a urinary bladder of a subject is displayed on a monitor in the first embodiment of the present invention.

In step S10, the urine volume measurement unit 13 extracts the urinary bladder region BR from each of the ultrasound images of the two measurement frames selected by the user in step S8 performed twice and calculates the volume of the urinary bladder B of the subject based on the diameters of the extracted urinary bladder region BR to measure the urine volume in the urinary bladder B. For example, the urine volume measurement unit 13 regards the urinary bladder B to be the ellipsoid E as illustrated in FIG. 7, measures the largest diameters LX, LY, and LZ respectively in the X, Y, and Z directions of the ellipsoid E from the ultrasound images of the two measurement frames selected by the user in step S8, and calculates $(LX \times LY \times LZ) \times \pi/6$. In this manner, the urine volume measurement unit 13 can calculate the volume of the ellipsoid E as the volume of the urinary bladder B. For example, as illustrated in FIG. 10, the urine volume measurement unit 13 displays a measured urine volume J in the urinary bladder B on the monitor 6. In the example of FIG. 10, the ultrasound image UD of the measurement frame selected by the user in the step S9 performed for the second time and the urine volume J in the urinary bladder B are displayed together on the monitor 6.

Figure 9:
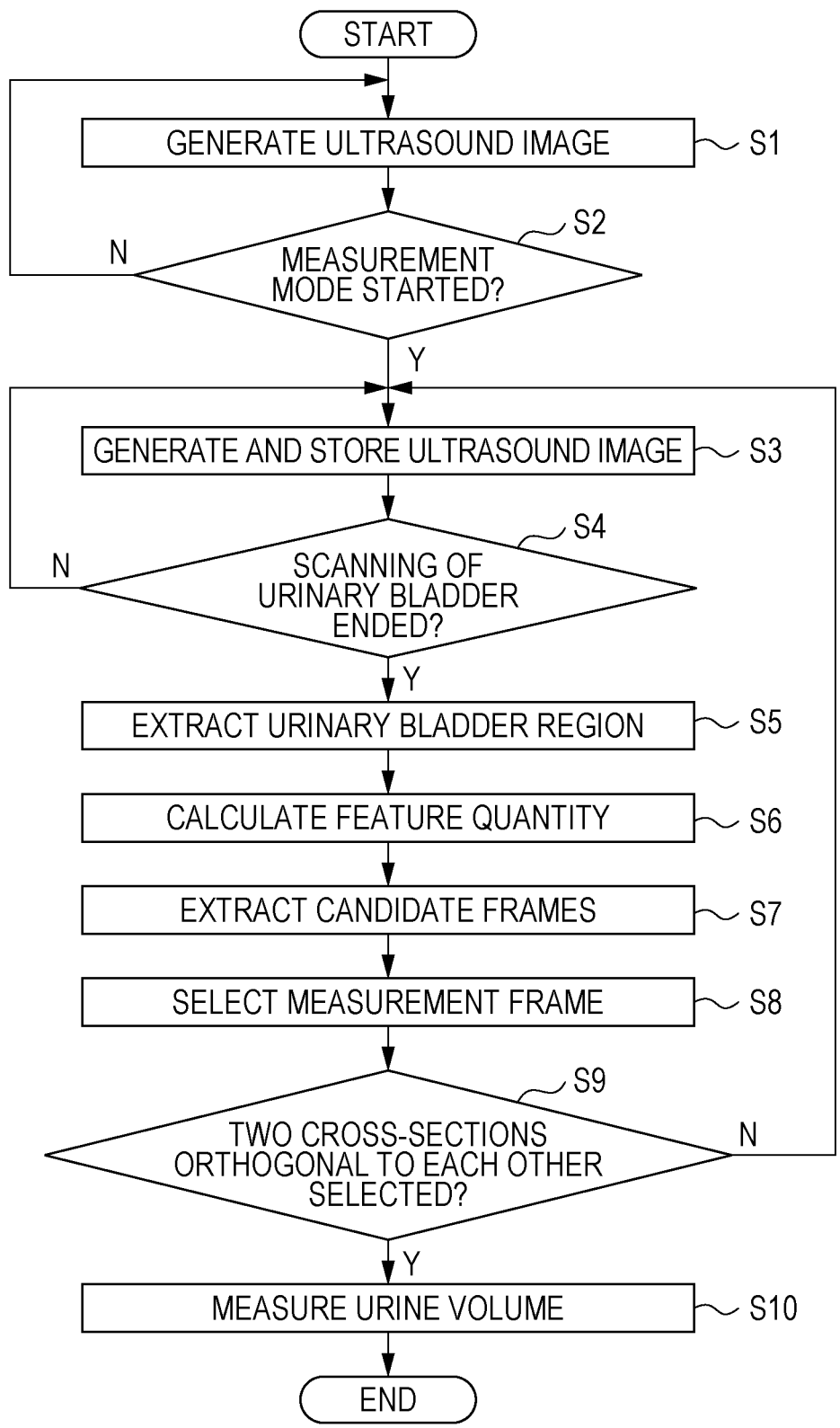
FIG. 9 is a flowchart illustrating an operation of the ultrasound diagnostic apparatus according to the first embodiment of the present invention.

In response to the urine volume in the urinary bladder B of the subject being measured in this manner, the operation of the ultrasound diagnostic apparatus 1 illustrated in the flowchart of FIG. 9 ends.

As described above, the ultrasound diagnostic apparatus 1 according to the first embodiment of the present invention calculates a feature quantity related to the urinary bladder region BR, such as the area of the urinary bladder region BR, in each of the ultrasound images of the plurality of frames stored in the image memory 7, extracts an ultrasound image of at least one frame for which the feature quantity becomes a local maximum as the ultrasound image of the at least one candidate frame, and selects the ultrasound image U2 of the frame selected by the user as the ultrasound image UD of the measurement frame from the ultrasound image UC of the at least one candidate frame displayed on the monitor 6. Thus, when selecting the ultrasound image UD of the measurement frame, the user need not check ultrasound images of many frames. Consequently, the ultrasound diagnostic apparatus according to the first embodiment of the present invention can reduce the load imposed on the user.

The ultrasound diagnostic apparatus 1 according to the first embodiment selects the ultrasound image U2 of the one frame selected by the user, as the ultrasound image UD of the measurement frame from the ultrasound image UC of the at least one candidate frame displayed on the monitor 6. Thus, even if the ultrasound image UC of the at least one candidate frame includes an ultrasound image of a frame in which the urinary bladder region BR is not correctly extracted, the ultrasound diagnostic apparatus 1 according to the first embodiment can select the ultrasound image UD of the measurement frame suitable for urine volume measurement, and can increase the accuracy of urine volume measurement.

The beamformer 26 that performs so-called reception focusing processing is included in the transmission/reception circuit 3. However, the beamformer 26 may be included in the image generation unit 4, for example. Even in this case, as in the case where the beamformer 26 is included in the transmission/reception circuit 3, an ultrasound image is generated by the image generation unit 4.

The image generation unit 4 is included in the processor 22. However, the image generation unit 4 may be included in the ultrasound probe 21.

It is determined in step S4 that scanning of the urinary bladder B is ended if an instruction for ending scanning of the urinary bladder B is given by the user. However, for example, it may be determined that scanning of the urinary bladder B is ended when a predetermined period such as 15 seconds, for example, has elapsed from a timing at which the measurement mode is started in step S2 and the generation and storage of the ultrasound image are started in step S3. In this case, the user's time of giving an instruction for ending scanning of the urinary bladder B can be saved.

For example, it may be determined whether or not the ultrasound probe 21 is in contact with the body surface S of the subject, and control may be performed to start and end scanning of the urinary bladder B in accordance with the determined result. When the ultrasound probe 21 is in contact with the body surface S of the subject, an ultrasound image of a frame corresponding to a scan cross-section of the subject is generated. By contrast, when the ultrasound probe 21 is separate from the subjected to be in a so-called aerial radiation state, an entirely black ultrasound image is usually generated. Thus, for example, by analyzing the generated ultrasound image, it can be determined whether or not the ultrasound probe 21 is in contact with the body surface S of the subject. Accordingly, for example, when it is determined that the ultrasound probe 21 is in contact with the body surface S of the subject, scanning of the urinary bladder B can be started, and when it is determined that the ultrasound probe 21 is separate from the body surface S of the subject, scanning of the urinary bladder B can be ended. In this case, the user's time of giving an instruction for ending scanning of the urinary bladder B can also be saved.

The above-described plurality of methods for determining the start and end of scanning of the urinary bladder B can be appropriately combined with each other.

After the ultrasound images of the plurality of frames are stored in the image memory 7, the processing of extracting the urinary bladder region BR is performed in step S5 on the ultrasound images of all the frames stored in the image memory 7. However, the processing of extracting the urinary bladder region BR may be performed sequentially on the ultrasound image of the frame stored in the image memory 7 while scanning of the urinary bladder B is continued in step S4.

If the processing of extracting the urinary bladder region BR is performed sequentially on the ultrasound image of the frame generated in step S3, the waiting time until storage of the ultrasound images of the plurality of frames in the image memory 7 ends can be decreased. Since the processing of calculating the feature quantity in step S6 can also be performed sequentially on the ultrasound image of the frame in which the urinary bladder region BR is extracted, the waiting time can be further decreased.

An example in which the user scans the urinary bladder B using the swing method has been described. Alternatively, a slide method in which the ultrasound probe 21 is translated on the body surface S of the subject while keeping the inclination angle of the ultrasound probe 21 constant can also be used for scanning the urinary bladder B.

Figure 11:
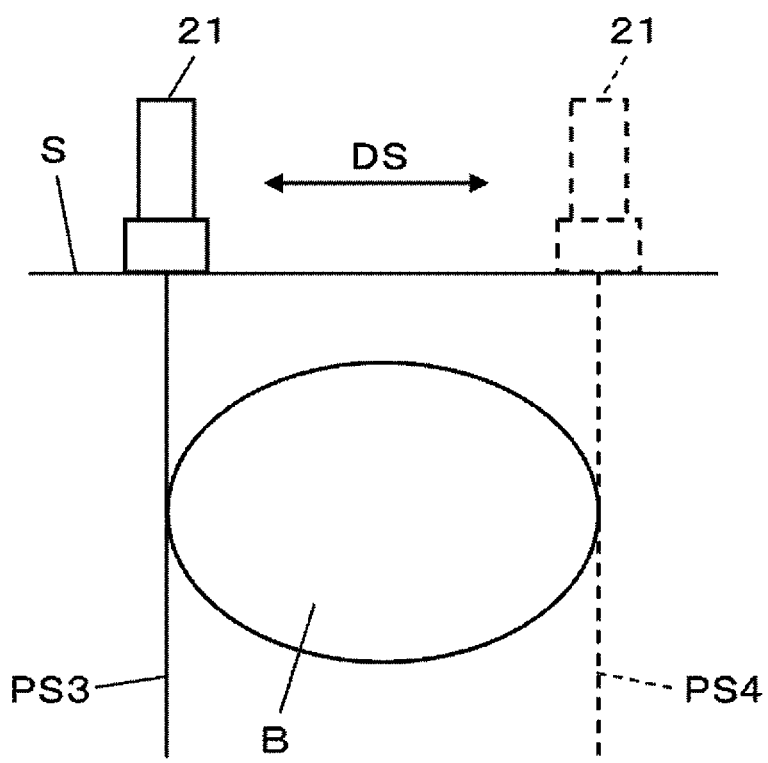
FIG. 11 is a diagram schematically illustrating how a urinary bladder is scanned using a slide method.

For example, as illustrated in FIG. 11, when the user scans the urinary bladder B using the slide method, the user moves the ultrasound probe 21 back and forth between a position at which a scan cross-section PS3 that passes through one end of the urinary bladder B in a sliding direction DS is imaged and a position at which a scan cross-section PS4 that passes through the other end of the urinary bladder B in the sliding direction DS is imaged, where the sliding direction DS is a direction in which the ultrasound probe 21 is translated on the body surface S of the subject.

In this case, the feature quantity such as the area of the urinary bladder region BR in the ultrasound images of the generated frames takes the local minimum values at the position of the ultrasound probe 21 where the scan cross-sections PS3 is imaged and at the position of the ultrasound probe 21 where the scan cross-sections PS4 is imaged, and takes the local maximum value at the position of the ultrasound probe 21 where a scan cross-section that passes through the center of the urinary bladder B is imaged. Thus, as in the case where the urinary bladder B is scanned using the swing method, the feature quantity of the urinary bladder region BR changes as illustrated in FIG. 6.

Thus, as in the case where the urinary bladder B is scanned using the swing method, the ultrasound images of the frames for which the feature quantity has the local maximum value can be extracted as the ultrasound images of the candidate frames also in the case where the urinary bladder B is scanned using the slide method. Thus, the accuracy of urine volume measurement can be increased while the load imposed on the user is reduced.

In step S7, the candidate frame extraction unit 11 may acquire the graph representing a time-series change of the feature quantity related to the urinary bladder region BR as illustrated in FIG. 6 and perform filtering processing using a so-called smoothing filter or low-pass filter on the curve of the acquired graph to be able to acquire a graph of a smooth curve. Consequently, the candidate frame extraction unit 11 can accurately detect the local maximum values M1 to M5 from the graph in which the influence of noise or the like is reduced through the filtering processing.

The operation of the ultrasound diagnostic apparatus 1 returns to step S3 if it is determined in step S9 that ultrasound images of two measurement frames corresponding to two scan cross-sections of the urinary bladder B of the subject orthogonal to each other are not selected. For example, immediately after step S9, a message prompting rotation of the orientation of the ultrasound probe 21 by 90° may be displayed on the monitor 6. If an instruction regarding an operation to be performed on the ultrasound probe 21 is given to the user in this manner, the user can more smoothly proceed with the procedure of urine volume measurement.

The user may select whether or not to redo urine volume measurement after urine volume measurement of the urinary bladder B is completed in step S10 and the measurement result is displayed on the monitor 6. At this time, if the user selects to redo urine volume measurement, the process returns to step S3 and urine volume measurement is performed again. If the user selects to end urine volume measurement, the operation of urine volume measurement ends. Urine volume measurement can be redone in this manner, so that urine volume measurement can be performed more accurately.

The image memory 7 stores the ultrasound images of the frames generated by the image generation unit 4. The image memory 7 can also store ultrasound images of a series of frames input from the outside. In this case, urine volume measurement can be performed based on the ultrasound images of the plurality of frames input from the outside instead of the ultrasound images of the frames generated by the image generation unit 4. Thus, in this case, the ultrasound diagnostic apparatus 1 need not include the ultrasound probe 21 including the transducer array 2 and the transmission/reception circuit 3, and the image generation unit 4.

Second Embodiment

In the first embodiment, the ultrasound image UD of the measurement frame is selected in accordance with an input operation performed by the user via the input device 15 from the ultrasound image UC of the at least one candidate frame. If the extracted ultrasound image UC of the candidate frame is of only a single frame, the extracted ultrasound image UC of the candidate frame can be automatically selected as the ultrasound image UD of the measurement frame, for example.

Figure 12:
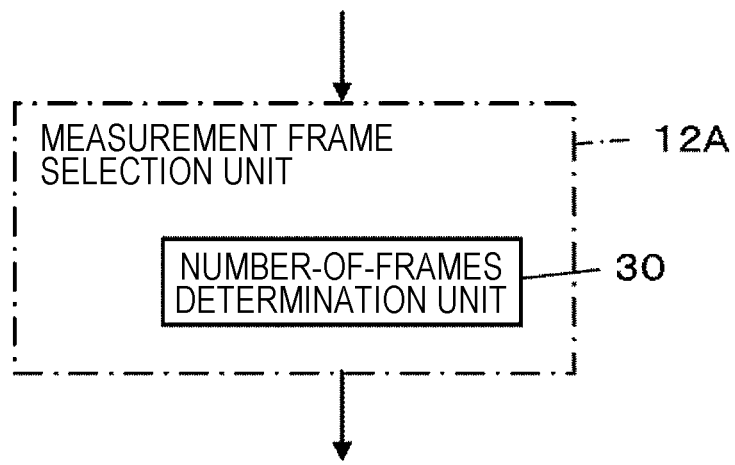
FIG. 12 is a block diagram illustrating an internal configuration of a measurement frame selection unit in a second embodiment of the present invention.

An ultrasound diagnostic apparatus according to a second embodiment is equivalent to the ultrasound diagnostic apparatus 1 according to the first embodiment illustrated in FIG. 1 that includes a measurement frame selection unit 12A illustrated in FIG. 12 instead of the measurement frame selection unit 12. The measurement frame selection unit 12A includes a number-of-frames determination unit 30.

The number-of-frames determination unit 30 determines whether or not the ultrasound images UC of the plurality of candidate frames are extracted by the candidate frame extraction unit 11.

The measurement frame selection unit 12A selects the ultrasound image UD of the measurement frame by taking into account the determined result obtained by the number-of-frames determination unit 30.

Figure 13:
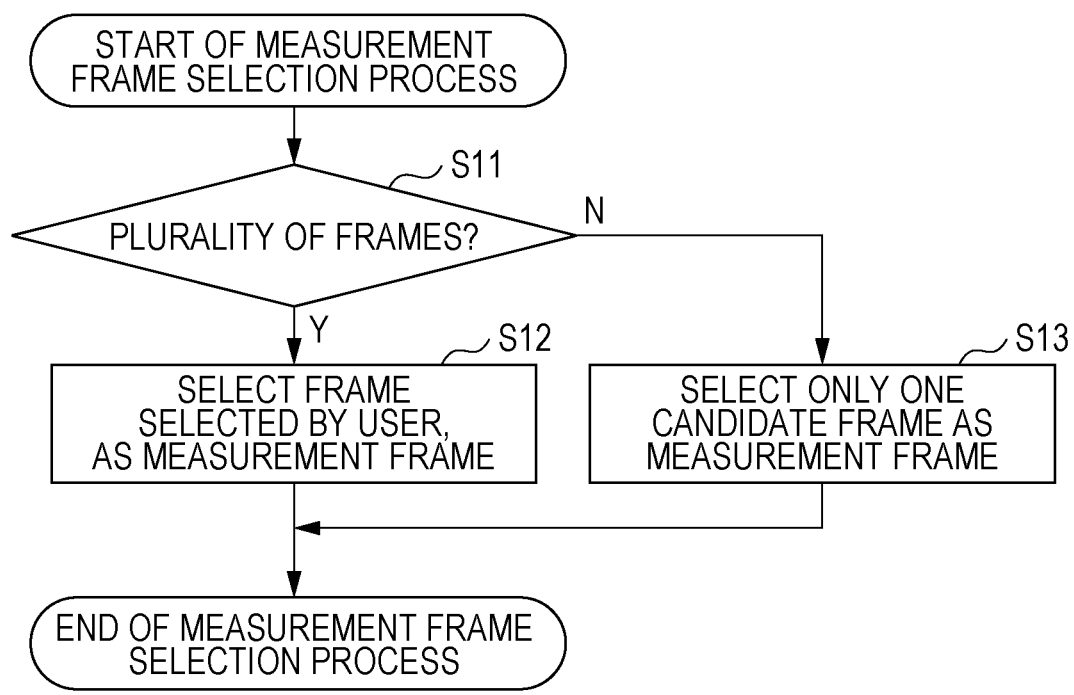
FIG. 13 is a flowchart illustrating an operation of selecting an ultrasound image of a measurement frame in the second embodiment of the present invention.

A specific operation performed when the measurement frame selection unit 12A selects the ultrasound image UD of the measurement frame will be described in detail using a flowchart illustrated in FIG. 13. In the second embodiment, the operation illustrated in the flowchart of FIG. 13 is performed instead of step S8 in the operation of the ultrasound diagnostic apparatus 1 according to the first embodiment illustrated in FIG. 9.

First, in step S11, the number-of-frames determination unit 30 of the measurement frame selection unit 12A receives the ultrasound image(s) of the candidate frame(s) extracted by the candidate frame extraction unit 11 and calculates the number of frames to determine whether ultrasound image of a plurality of candidate frames are extracted by the candidate frame extraction unit 11 or an ultrasound image of only one candidate frame is extracted by the candidate frame extraction unit 11.

If it is determined in step S11 that ultrasound images of a plurality of candidate frames are extracted by the candidate frame extraction unit 11, the process proceeds to step S12.

In step S12, the measurement frame selection unit 12A selects the ultrasound image of the frame selected by the user via the input device 15, as the ultrasound image UD of the measurement frame from among the ultrasound images UC of the plurality of candidate frames displayed on the monitor 6, as in step S8 of the operation of the ultrasound diagnostic apparatus 1 according to the first embodiment.

If it is determined in step S11 that an ultrasound image of only one candidate frame is extracted by the candidate frame extraction unit 11, the process proceeds to step S13.

In step S13, the measurement frame selection unit 12A automatically selects the ultrasound image UC of the only one candidate frame extracted by the candidate frame extraction unit 11 as the ultrasound image UD of the measurement frame.

In response to completion of the processing of step S12 or S13 in this manner, the operation of selecting the ultrasound image UD of the measurement frame illustrated in the flowchart of FIG. 13 is completed.

As described above, when the ultrasound image UC of only one candidate frame is extracted by the candidate frame extraction unit 11, the ultrasound diagnostic apparatus according to the second embodiment automatically selects the ultrasound image UC of the only one candidate frame as the ultrasound image UD of the measurement frame. Thus, the ultrasound diagnostic apparatus according to the second embodiment can reduce the load imposed on the user who selects the ultrasound image UD of the measurement frame.

Figure 14:
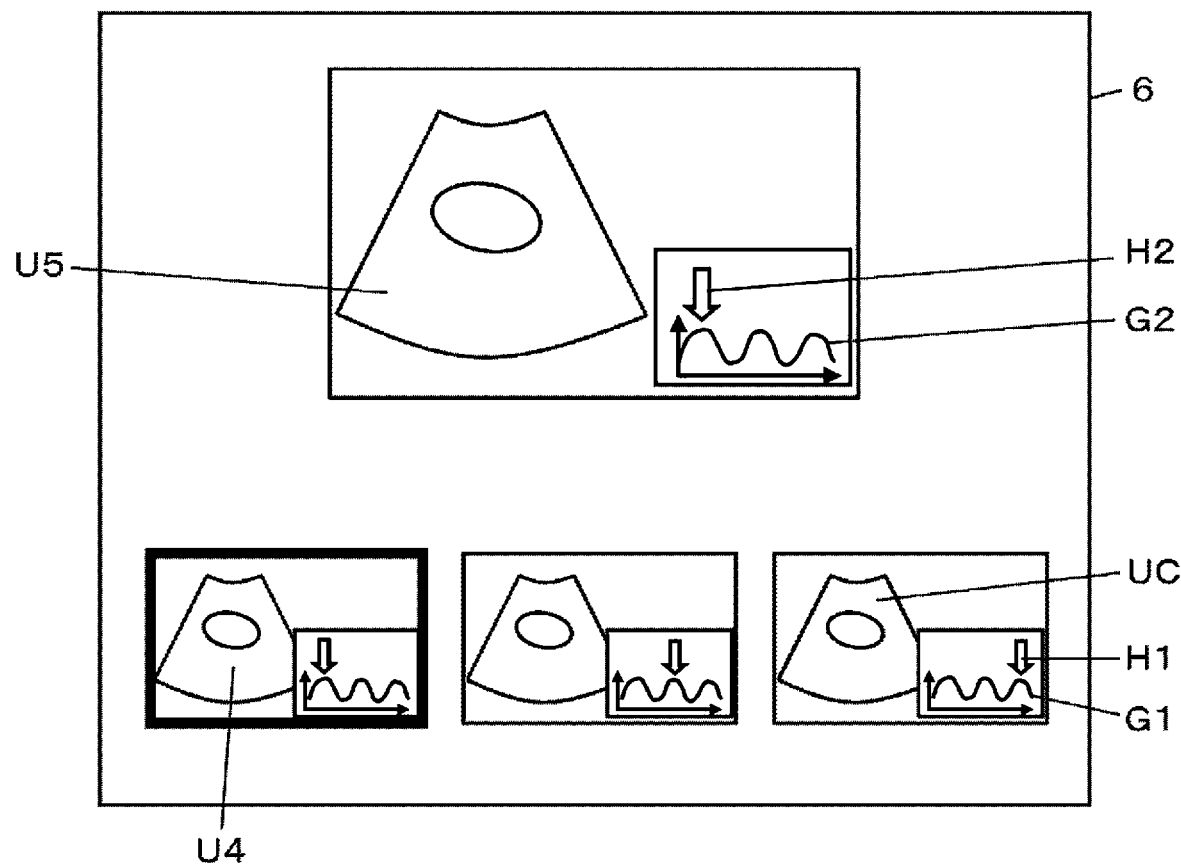
FIG. 14 is a diagram schematically illustrating an example of ultrasound images of a plurality of candidate frames and graphs displayed in the second embodiment of the present invention.

In the second embodiment, if the number-of-frames determination unit 30 determines that the ultrasound images UC of the plurality of candidate frames are extracted by the candidate frame extraction unit 11, the user selects an ultrasound image of one frame from among the ultrasound images UC of the plurality of candidate frames displayed on the monitor 6. At this time, to assist the user in making a determination, for example, the candidate frame extraction unit 11 can display, for each of the ultrasound images UC of the plurality of candidate frames, a graph G1 that represents a time-series change of the feature quantity and in which a marker H1 representing a time-series position of the ultrasound image UC of the candidate frame is placed as illustrated in FIG. 14. In the example of FIG. 14, the ultrasound images UC of three candidate frames are displayed in a lower portion of the monitor 6, an ultrasound image U4 at the leftmost position is selected by the user, and an ultrasound image U5 that is the enlarged ultrasound image U4 of the frame selected by the user is displayed in an upper portion of the monitor 6 together with an enlarged graph G2 and an enlarged marker H2.

Although an illustration is omitted, the candidate frame extraction unit 11 may display, on the monitor 6, a value of the feature quantity for each of the ultrasound images UC of the candidate frames together with the ultrasound image UC of the candidate frame.

If at least one of the graph G1 representing a time-series change of the feature quantity or the value of the feature quantity is displayed together with each of the ultrasound images UC of the candidate frames in this manner, it becomes easier for the user to select the ultrasound image UD of the measurement frame suitable from urine volume measurement from among the ultrasound images UC of the plurality of candidate frames. Thus, the accuracy of urine volume measurement can be increased.

Regardless of whether the ultrasound images UC of a plurality of candidate frames are extracted or the ultrasound image UC of only one candidate frame is extracted by the candidate frame extraction unit 11, the ultrasound image(s) UC of all the candidate frame(s) extracted by the candidate frame extraction unit 11 is (are) displayed on the monitor 6. However, for example, if the number-of-frames determination unit 30 determines that the ultrasound image UC of only one candidate frame is extracted, displaying of the ultrasound image UC of the candidate frame on the monitor 6 can be skipped.

Third Embodiment

There may be a case where, when the feature quantity calculated by the feature quantity calculation unit 10 has a plurality of local maximum values in the time-series change, the plurality of local maximum values may include an outlier that is a markedly large value or a markedly small value because the urinary bladder region BR is not correctly extracted or the like. Thus, for example, processing of removing an ultrasound image of a frame that has an outlier of the feature quantity from the ultrasound images UC of the plurality of candidate frames can be performed.

Figure 15:
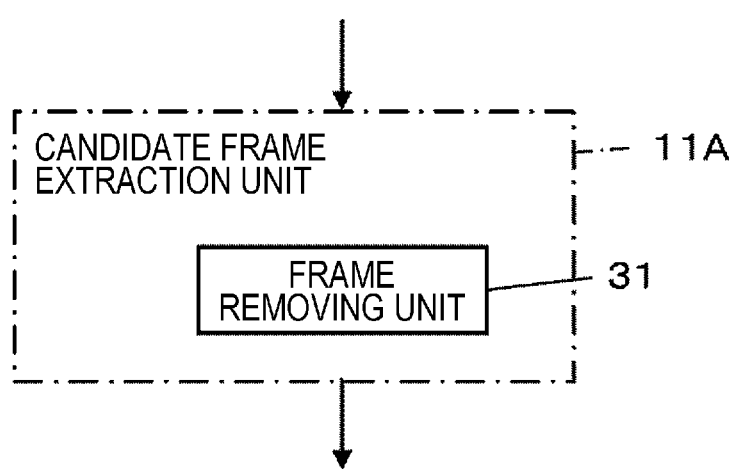
FIG. 15 is a block diagram illustrating an internal configuration of a candidate frame extraction unit in a third embodiment of the present invention.

An ultrasound diagnostic apparatus according to a third embodiment is equivalent to the ultrasound diagnostic apparatus 1 according to the first embodiment illustrated in FIG. 1 that includes a candidate frame extraction unit 11A illustrated in FIG. 15 instead of the candidate frame extraction unit 11. The candidate frame extraction unit 11A includes a frame removing unit 31.

The frame removing unit 31 removes an ultrasound image of a frame having an outlier of the feature quantity from the ultrasound images UC of the plurality of candidate frames extracted by the candidate frame extraction unit 11A.

At this time, for example, the frame removing unit 31 analyzes the time-series change of the feature quantity calculated by the feature quantity calculation unit 10 and calculates a maximum value among a plurality of local maximum values of the feature quantity. The frame removing unit 31 multiplies the calculated maximum value by a predetermined ratio that is greater than 0 and less than 1, for example, to set a feature quantity threshold determined relative to the maximum value such that the feature quantity threshold is a value smaller than the maximum value. The frame removing unit 31 can remove an ultrasound image of a frame having a local maximum value that is smaller than the feature quantity threshold among the plurality of local maximum values of the feature quantity, from the ultrasound images UC of the plurality of candidate frames.

As described above, if an ultrasound image of a frame for which the feature quantity is an outlier is removed from the ultrasound images UC of the plurality of candidate frames, only the ultrasound image(s) UC of the normal candidate frame(s) is (are) displayed on the monitor 6 and the ultrasound image UD of the measurement frame is selected. Thus, the ultrasound diagnostic apparatus according to the third embodiment can further reduce the load imposed on the user in selecting the ultrasound image UD of the measurement frame and can increase the accuracy of urine volume measurement.

For example, the frame removing unit 31 may remove an ultrasound image by using an average value of the local maximum values of the feature quantity in the ultrasound images of the frames for which the feature quantity calculated by the feature quantity calculation unit 10 becomes a local maximum. In this case, for example, the frame removing unit 31 analyzes a time-series change of the feature quantity calculated by the feature quantity calculation unit 10, and calculates an average value of the plurality of local maximum values of the feature quantity and a standard deviation of the feature quantity. The frame removing unit 31 then sets a feature quantity range determined relative to the average value of the local maximum values of the feature quantity such that the feature quantity range has, as a lower-limit value, a value obtained by subtracting a product of the standard deviation and a certain ratio from the average value and has, as an upper-limit value, a value obtained by adding the product of the standard deviation and the certain ratio to the average value. The frame removing unit 31 can remove an ultrasound image of a frame having a local maximum value of the feature quantity that is out of the feature quantity range among the plurality of local maximum values of the feature quantity, from the ultrasound images UC of the plurality of candidate frames.

Description is given such that the configuration of the third embodiment is applied to the first embodiment. However, the configuration of the third embodiment is similarly applied to the second embodiment.

Fourth Embodiment

There may be a case where the urinary bladder region BR is not correctly extracted and thus the feature quantity is not correctly calculated because of movement of the ultrasound probe 21 that is not usually performed in scanning of the urinary bladder B such as a shift in the position of the ultrasound probe 21 while the user is scanning the urinary bladder B or strong pressing of the ultrasound probe 21 against the body surface S of the subject to avoid gas accumulated in the abdomen of the subject. An ultrasound image of a frame generated, in scanning of the urinary bladder B, in response to such movement of the ultrasound probe 21 that is not usually performed may be removed from the ultrasound images UC of the plurality of candidate frames.

An ultrasound diagnostic apparatus according to the fourth embodiment has the same configuration as the ultrasound diagnostic apparatus according to the third embodiment.

When the urinary bladder B is scanned using the swing method or the slide method, the area of the urinary bladder region BR usually changes in time series to alternately have the local maximum values M1 to M5 and the local minimum values N1 to N4 as illustrated in FIG. 6 and differences between a local maximum value and a local minimum value that are adjacent to each other in time series are within a certain range. On the other hand, when there is movement of the ultrasound probe 21 that is not usually performed in scanning of the urinary bladder B, differences between a local maximum value and a local minimum value that are adjacent to each other in time series may be smaller than the certain range as illustrated in FIG. 16, for example.

Figure 16:
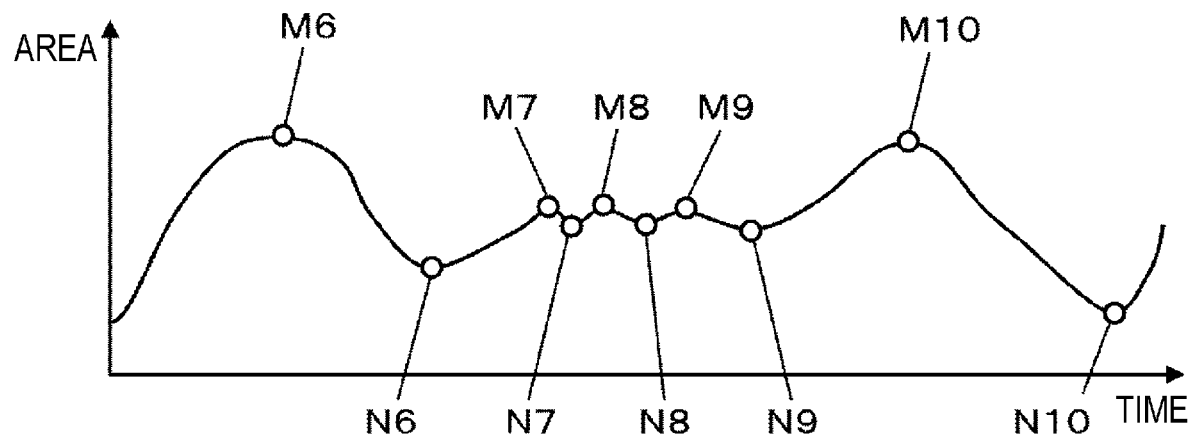
FIG. 16 is a diagram illustrating an example of a time-series change of an area of a urinary bladder region in the third embodiment of the present invention.

In the example of FIG. 16, in a section from a generation time of an ultrasound image of a frame having a local maximum value M7 to a generation time of an ultrasound image of a frame having a local minimum value N9, differences between a local maximum value and a local minimum value that are adjacent to each other in time series are smaller than differences between a local maximum value and a local minimum value that are adjacent to each other in time series in the other sections, for example. Thus, the ultrasound images of the frames having the local maximum values M7 to M9 of the feature quantity can be estimated to be ultrasound images of frames generated, in scanning of the urinary bladder B, in response to movement of the ultrasound probe 21 that is not usually performed in scanning of the urinary bladder B.

In the fourth embodiment, the frame removing unit 31 has a predetermined difference threshold for the differences between the local maximum values M6 to M10 and the local minimum values N6 to N10. The frame removing unit 31 analyzes a time-series change of the feature quantity calculated by the feature quantity calculation unit 10 and calculates differences between the local maximum values M6 to M10 and the local minimum values N6 to N10 that are adjacent to each other in time series. If the calculated difference is smaller than the predetermined difference threshold, the frame removing unit 31 removes an ultrasound image of a frame having that local maximum value from the ultrasound images of the plurality of candidate frames.

In the example of FIG. 16, the frame removing unit 31 extracts ultrasound images of five frames for which the feature quantity has the local maximum values M6 to M10, as the ultrasound images UC of the candidate frames, and calculates differences between the local maximum values M6 to M10 and the respective adjacent local minimum values N6 to N10 in time series. If the differences between the local maximum values M7 to M9 of the feature quantity and the respective adjacent local minimum values N7 to N9 in time series are smaller than the predetermined difference threshold, the frame removing unit 31 removes the ultrasound images of the three frames having the local maximum values M7 to M9 from the ultrasound images UC of the five candidate frames.

As described above, since the ultrasound diagnostic apparatus according to the fourth embodiment can constitute the ultrasound images UC of the plurality of candidate frames by ultrasound images of frames generated through normal scanning of the urinary bladder B, it is more likely that the ultrasound image UD of the measurement frame suitable for urine volume measurement is selected from among the ultrasound images UC of the plurality of candidate frames. Thus, the ultrasound diagnostic apparatus according to the fourth embodiment can further reduce the load imposed on the user and increase the accuracy of urine volume measurement.

Fifth Embodiment

In the first embodiment, when the ultrasound images UC of the plurality of candidate frames are extracted by the candidate frame extraction unit 11, the ultrasound images UC of the plurality of candidate frames can be sorted based on a certain criterion and the sorted ultrasound images UC can be displayed on the monitor 6 to make it easier for the user to select the ultrasound image UD of the measurement frame from among the ultrasound images UC of the plurality of candidate frames.

Figure 17:
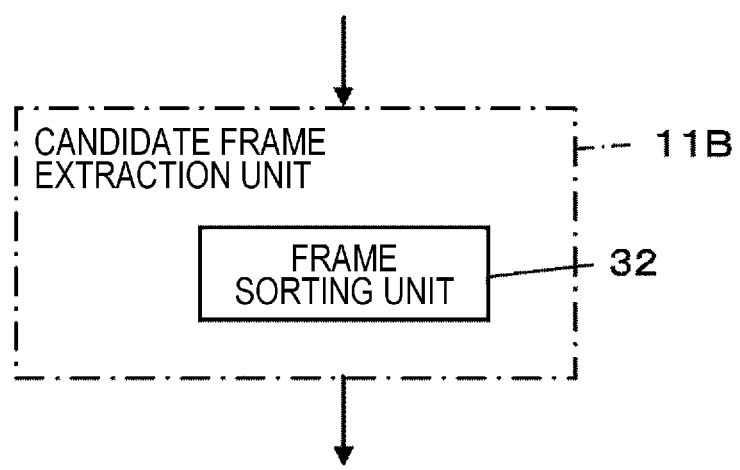
FIG. 17 is a block diagram illustrating an internal configuration of a candidate frame extraction unit in a fifth embodiment of the present invention.

An ultrasound diagnostic apparatus according to a fifth embodiment is equivalent to the ultrasound diagnostic apparatus 1 according to the first embodiment illustrated in FIG. 1 that includes a candidate frame extraction unit 11B illustrated in FIG. 17 instead of the candidate frame extraction unit 11. The candidate frame extraction unit 11B includes a frame sorting unit 32.

When the urinary bladder B is scanned using the swing method or the slide method, it is considered that an ultrasound image of a frame for which the feature quantity such as the area or largest diameter of the urinary bladder region BR calculated by the feature quantity calculation unit 10 becomes a local maximum corresponds to a scan cross-section that passes through the vicinity of the center of the urinary bladder B and the ultrasound image corresponds to a scan cross-section that passes a portion closer to the center of the urinary bladder B as the value of the feature quantity becomes larger.

Thus, for example, to make it easier for the user to select an ultrasound image of a frame suitable for urine volume measurement, the frame sorting unit 32 sorts the ultrasound images UC of the plurality of candidate frames extracted by the candidate frame extraction unit 11B in descending order of the feature quantity such as the area or largest diameter of the urinary bladder region BR, and displays the sorted ultrasound images UC of the plurality of candidate frames on the monitor 6.

As described above, the ultrasound diagnostic apparatus according to the fifth embodiment can sort the ultrasound images UC of the plurality of candidate frames based on a certain criterion and display the sorted ultrasound images of the plurality of candidate frames on the monitor 6. Thus, it becomes easier for the user to select the ultrasound image UD of the suitable measurement frame from among the ultrasound images UC of the plurality of candidate frames, and the accuracy of urine volume measurement can be increased.

Conceivable indices for use in determining whether or not the urinary bladder region BR is correctly depicted in an ultrasound image may be, for example, a roundness of the urinary bladder region BR and an edge clarity of the urinary bladder region BR. The roundness of the urinary bladder region BR is an index that has a larger value as the shape of the urinary bladder region BR is a circular shape and has a smaller value as the shape of the urinary bladder region BR is a non-circular shape. The edge clarity of the urinary bladder region BR is an index value that has a larger value as the outline of the bladder region BR becomes clear and has a smaller value as the outline of the bladder region BR becomes unclear. As the roundness or the edge clarity of the urinary bladder region BR becomes larger, it can be determined that the urinary bladder region BR is depicted more correctly in the ultrasound image. As the roundness or the edge clarity of the urinary bladder region BR becomes smaller, it can be determined that urinary bladder region BR is not depicted correctly in the ultrasound image because of some reason.

Thus, for example, instead of sorting the ultrasound images UC of the plurality of candidate frames using the feature quantity, the frame sorting unit 32 may analyze the ultrasound images UC of the plurality of candidate frames to calculate, as the index value, the roundness or the edge clarity of the urinary bladder region BR in the ultrasound images UC of the plurality of candidate frames and sort the ultrasound images UC of the plurality of candidate frames in descending order of the calculated index value. In this case, it is easier for the user to select an ultrasound image of a frame in which the urinary bladder region BR is correctly depicted from among the ultrasound images UC of the plurality of candidate frames, and the accuracy of urine volume measurement can be increased.

For example, the frame sorting unit 32 can perform sorting using the feature quantity and sorting using the index value in combination. In this case, for example, the frame sorting unit 32 sorts the ultrasound images UC of the plurality of candidate frames in descending order of the feature quantity and then divides the sorted ultrasound images of the plurality of candidate frames into groups of a certain number of frames such as three frames. In each of the groups of the candidate frames, the frame sorting unit 32 sorts the ultrasound images in descending order of the index. Thus, the frame sorting unit 32 can sort the ultrasound images UC of the plurality of candidate frames such that the plurality of groups in the ultrasound images UC of the candidate frames are sorted in descending order of the feature quantity and the ultrasound images UC of the plurality of candidate frame in each of the groups are sorted in descending order of the index value.

In this case, the user can select the ultrasound image UD of the measurement frame from among the ultrasound images UC of the plurality of candidate frames by taking into account both the feature quantity and the index value related to the urinary bladder region BR. Thus, it becomes easier for the user to select the ultrasound image UD of the suitable measurement frame, and the accuracy of urine volume measurement can be increased.

When the urinary bladder B is scanned using the swing method, the ultrasound probe 21 is usually placed at a position determined by the user that the largest urinary bladder region BR is depicted, and the ultrasound probe 21 is inclined at the position. Thus, for example, when an inclination angle is set such that the inclination angle of the ultrasound probe 21 in a state in which the ultrasound probe 21 is oriented in a direction perpendicular to the body surface S of the subject is 0 and the inclination angle increases as the ultrasound probe 21 is inclined more, it can be estimated that an ultrasound image of a frame generated in a state in which the inclination angle is close to 0 corresponds to a scan cross-section that passes through the vicinity of the center of the urinary bladder B.

Thus, an angle sensor (not illustrated) for detecting the inclination angle of the ultrasound probe 21 may be attached to the ultrasound probe 21, and the value of the inclination angle of the ultrasound probe 21 detected by the angle sensor may be used as an index value for use in sorting the ultrasound images UC of the plurality of candidate frames. The angle sensor includes, for example, a so-called gyro sensor, an acceleration sensor, a magnetic sensor, or the like. The angle sensor converts an electric signal obtained from the gyro sensor, the acceleration sensor, the magnetic sensor, or the like into the inclination angle of the ultrasound probe 21 by using a well-known calculation method or the like.

If the ultrasound images UC of the plurality of candidate frames are sorted using the inclination angle of the ultrasound probe 21 as the index value, it becomes easier for the user to select an ultrasound image of a frame suitable for urine volume measurement, and the accuracy of urine volume measurement can be increased.

The description has been given such that the configuration of the fifth embodiment is applied to the first embodiment. However, the configuration of the fifth embodiment is similarly applied to the second to fourth embodiments.

Sixth Embodiment

The ultrasound diagnostic apparatus 1 according to the first embodiment has a configuration in which the monitor 6, the input device 15, and the ultrasound probe 21 are directly connected to the processor 22. However, for example, the monitor 6, the input device 15, the ultrasound probe 21, and the processor 22 may be connected indirectly to each other via a network.

Figure 18:
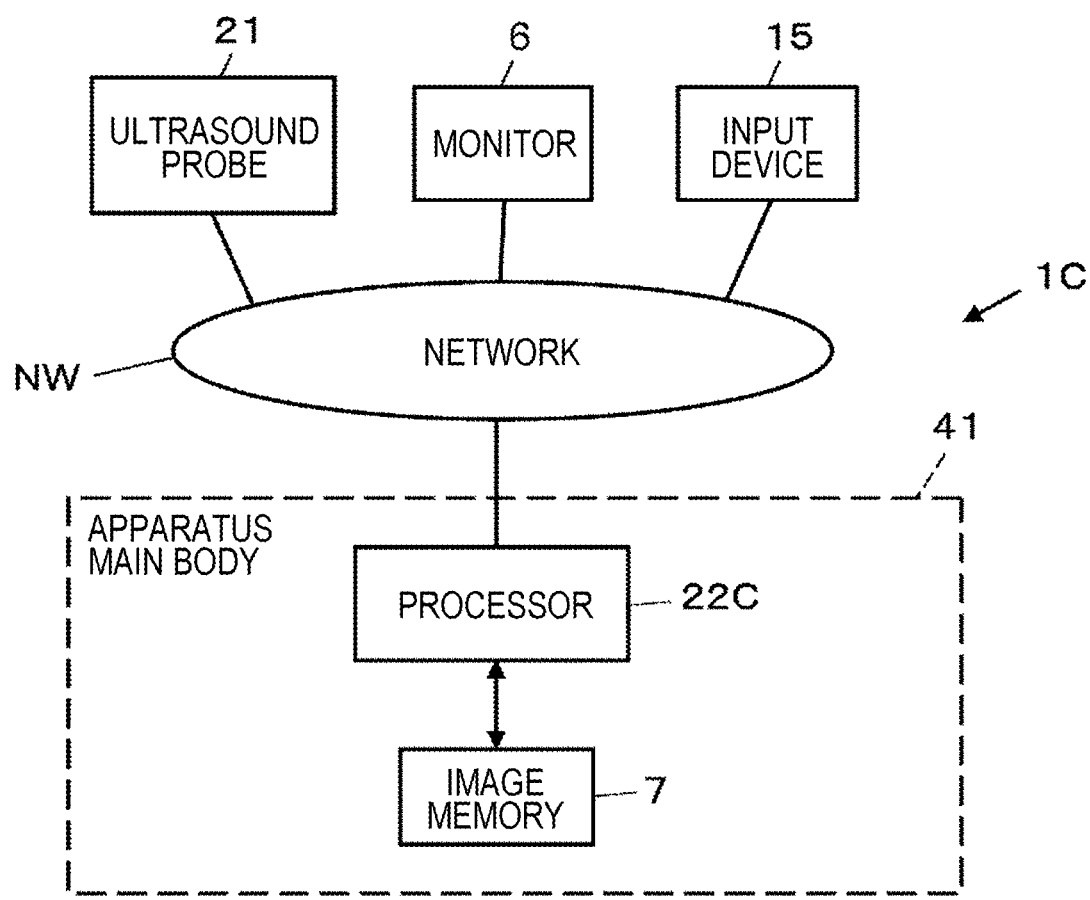
FIG. 18 is a block diagram illustrating a configuration of an ultrasound diagnostic apparatus according to a sixth embodiment of the present invention.

As illustrated in FIG. 18, in an ultrasound diagnostic apparatus 1C according to a sixth embodiment, the monitor 6, the input device 15, and the ultrasound probe 21 are connected to an ultrasound diagnostic apparatus main body 41 via a network NW. The ultrasound diagnostic apparatus main body 41 is equivalent to the ultrasound diagnostic apparatus 1 according to the first embodiment illustrated in FIG. 1 from which the monitor 6, the input device 15, and the ultrasound probe 21 are omitted, and is constituted by the image memory 7 and a processor 22C.

Similarly to the ultrasound diagnostic apparatus 1 according to the first embodiment, even the ultrasound diagnostic apparatus 1C having such a configuration calculates a feature quantity related to the urinary bladder region BR, such as the area of the urinary bladder region BR, in each of the ultrasound images of the plurality of frames stored in the image memory 8, extracts an ultrasound image of at least one frame for which the feature quantity becomes a local maximum as the ultrasound image of the at least one candidate frame, and selects the ultrasound image U2 of the frame selected by the user as the ultrasound image UD of the measurement frame from the ultrasound image UC of the at least one candidate frame displayed on the monitor 6. Thus, when selecting the ultrasound image UD of the measurement frame, the user need not check ultrasound images of many frames. Consequently, the ultrasound diagnostic apparatus can reduce the load imposed on the user. Even if the ultrasound image UC of the at least one candidate frame includes an ultrasound image of a frame in which the urinary bladder region BR is erroneously detected, the ultrasound image UD of the measurement frame suitable for urine volume measurement can be selected and the accuracy of urine volume measurement can be increased.

Since the monitor 6, the input device 15, and the ultrasound probe 21 are connected to the ultrasound diagnostic apparatus main body 41 via the network NW, the ultrasound diagnostic apparatus main body 41 can be used as a so-called remote server. Thus, for example, the user can examine the subject by preparing the monitor 6, the input device 15, and the ultrasound probe 21, so that convenience at the time of ultrasonic diagnosis can be improved.

For example, when a thin portable computer called a tablet is used as the monitor 6 and the input device 15, the user can more easily perform urine volume measurement. Thus, convenience of the urine volume measurement can be further improved.

The monitor 6, the input device 15, and the ultrasound probe 21 are connected to the ultrasound diagnostic apparatus main body 41 via the network NW. At this time, the monitor 6, the input device 15, and the ultrasound probe 21 may be connected to the network NW with cables or wirelessly.

The description has been given such that the configuration of the sixth embodiment is applied to the first embodiment. However, the configuration of the sixth embodiment is similarly applied to the second to fifth embodiments.

REFERENCE SIGNS LIST 1, 1C ultrasound diagnostic apparatus
2 transducer array
3 transmission/reception circuit
4 image generation unit
5 display control unit
6 monitor
7 image memory
9 urinary bladder extraction unit
10 feature quantity calculation unit
11, 11A, 11B candidate frame extraction unit
12, 12A measurement frame selection unit
13 urine volume measurement unit
14 device control unit
15 input device
21 ultrasound probe
22, 22A processor
23 puller
24 amplifier
25 AD converter
26 beamformer
27 signal processing unit
28 DSC
29 image processing unit
30 number-of-frames determination unit
31 frame removing unit
32 frame sorting unit
41 ultrasound diagnostic apparatus main body
B urinary bladder
BR urinary bladder region
DS sliding direction
ellipsoid
G1, G2 graph
H1, H2 marker
J urine volume
LX, LY, LZ largest diameter
M1 to M10 local maximum value
N1 to N4, N6 to N10 local minimum value
NW network
PS1, PS2, PS3, PS4 scan cross-section
R rotational axis
S body surface
U1 to U5, UC, UD ultrasound image

What is claimed is:

1. An ultrasound diagnostic apparatus comprising:
an image memory configured to store ultrasound images of a plurality of frames;
a processor configured to
extract a urinary bladder region from each of the ultrasound images of the plurality of frames,
calculate a feature quantity related to the urinary bladder region extracted for each of the ultrasound images of the plurality of frames,
extract, from the ultrasound images of the plurality of frames, an ultrasound image of a frame for which the feature quantity becomes a local maximum, as an ultrasound image of at least one candidate frame that serves as a candidate subjected to measurement,
select an ultrasound image of a measurement frame that serves as a target subjected to measurement from the ultrasound image of the at least one candidate frame, and
analyze the ultrasound image of the measurement frame which is selected to measure a urine volume.

2. The ultrasound diagnostic apparatus according to claim 1, wherein in a case where a difference between a local maximum value of the feature quantity in the ultrasound image of the frame for which the feature quantity becomes the local maximum and a local minimum value of the feature quantity adjacent to the local maximum value in time series is smaller than a predetermined difference threshold, the processor is further configured to remove the ultrasound image of the frame for which the feature quantity becomes the local maximum from the ultrasound image of the at least one candidate frame.

3. The ultrasound diagnostic apparatus according to claim 2, further comprising:
a monitor, wherein
the processor is further configured to display the ultrasound image of the at least one candidate frame on the monitor.

4. The ultrasound diagnostic apparatus according to claim 1, wherein the processor is further configured to remove, from the ultrasound image of the at least one candidate frame, an ultrasound image of a frame having a local maximum value of the feature quantity that is smaller than a feature quantity threshold determined relative to a maximum value of the feature quantity in ultrasound images of frames for each of which the feature quantity becomes a local maximum.

5. The ultrasound diagnostic apparatus according to claim 4, further comprising:
a monitor, wherein
the processor is further configured to display the ultrasound image of the at least one candidate frame on the monitor.

6. The ultrasound diagnostic apparatus according to claim 1, wherein the processor is further configured to remove, from the ultrasound image of the at least one candidate frame, an ultrasound image of a frame having a local maximum value of the feature quantity that is outside a feature quantity range determined relative to an average value of local maximum values of the feature quantity in ultrasound images of frames for each of which the feature quantity becomes a local maximum.

7. The ultrasound diagnostic apparatus according to claim 6, further comprising:
a monitor, wherein
the processor is further configured to display the ultrasound image of the at least one candidate frame on the monitor.

8. The ultrasound diagnostic apparatus according to claim 1, further comprising:
a monitor, wherein
the processor is further configured to display the ultrasound image of the at least one candidate frame on the monitor.

9. The ultrasound diagnostic apparatus according to claim 8, wherein
the extracted ultrasound image of the at least one candidate frame includes extracted ultrasound images of one or more candidate frames, and
the processor is further configured to display each of the extracted ultrasound images of the one or more candidate frames and a value of the feature quantity corresponding to the ultrasound image of the candidate frame, on the monitor.

10. The ultrasound diagnostic apparatus according to claim 8, further comprising:
an input device configured to accept an input operation of a user, wherein
the processor is further configured to select, as the ultrasound image of the measurement frame, an ultrasound image of a frame selected by the user via the input device from the ultrasound image of the at least one candidate frame displayed on the monitor.

11. The ultrasound diagnostic apparatus according to claim 8, further comprising:
an input device configured to accept an input operation of a user, wherein
the processor is further configured to
determine whether or not ultrasound images of a plurality of candidate frames are extracted,
in a case of determining that ultrasound images of a plurality of candidate frames are extracted, select, as the ultrasound image of the measurement frame, an ultrasound image of a frame selected by the user via the input device from the ultrasound images of the plurality of candidate frames displayed on the monitor, and
in a case of determining that an ultrasound image of only one candidate frame is extracted, select the ultrasound image of the only one candidate frame as the ultrasound image of the measurement frame.

12. The ultrasound diagnostic apparatus according to claim 8, wherein
the extracted ultrasound image of the at least one candidate frame includes extracted ultrasound images of one or more candidate frames, and
the processor is further configured to display each of the extracted ultrasound images of the one or more candidate frames and a graph that represents a time-series change in the feature quantity and in which a marker representing a time-series position corresponding to the ultrasound image of the candidate frame is placed, on the monitor.

13. The ultrasound diagnostic apparatus according to claim 12, wherein
the processor is further configured to display each of the extracted ultrasound images of the one or more candidate frames and a value of the feature quantity corresponding to the ultrasound image of the candidate frame, on the monitor.

14. The ultrasound diagnostic apparatus according to claim 8, wherein
the extracted ultrasound image of the at least one candidate frame includes extracted ultrasound images of one or more candidate frames, and
the processor is further configured to
calculate, as an index value, a roundness of the urinary bladder region or an edge clarity of the urinary bladder region for each of the extracted ultrasound images of the one or more candidate frames,
sort the ultrasound images of the one or more candidate frames based on the calculated index value, and
display the sorted ultrasound images of the one or more candidate frames on the monitor.

15. The ultrasound diagnostic apparatus according to claim 14, wherein
the processor is further configured to display each of the extracted ultrasound images of the one or more candidate frames and a value of the feature quantity corresponding to the ultrasound image of the candidate frame, on the monitor.

16. The ultrasound diagnostic apparatus according to claim 14, further comprising:
an input device configured to accept an input operation of a user, wherein
the processor is further configured to select, as the ultrasound image of the measurement frame, an ultrasound image of a frame selected by the user via the input device from the ultrasound image of the at least one candidate frame displayed on the monitor.

17. The ultrasound diagnostic apparatus according to claim 14, wherein
the extracted ultrasound image of the at least one candidate frame includes extracted ultrasound images of one or more candidate frames, and
the processor is further configured to display each of the extracted ultrasound images of the one or more candidate frames and a graph that represents a time-series change in the feature quantity and in which a marker representing a time-series position corresponding to the ultrasound image of the candidate frame is placed, on the monitor.

18. The ultrasound diagnostic apparatus according to claim 17, wherein
the processor is further configured to display each of the extracted ultrasound images of the one or more candidate frames and a value of the feature quantity corresponding to the ultrasound image of the candidate frame, on the monitor.

19. A method for controlling an ultrasound diagnostic apparatus, comprising:

extracting a urinary bladder region from each of ultrasound images of a plurality of frames;

calculating a feature quantity related to the urinary bladder region extracted for each of the ultrasound images of the plurality of frames;

extracting, from the ultrasound images of the plurality of frames, an ultrasound image of a frame for which the calculated feature quantity becomes a local maximum, as an ultrasound image of at least one candidate frame that serves as a candidate subjected to measurement;

selecting an ultrasound image of a measurement frame that serves as a target subjected to measurement from the ultrasound image of the at least one candidate frame; and analyzing the selected ultrasound image of the measurement frame to measure a urine volume.

* * * * *